United States Patent
Aoki et al.

(10) Patent No.: US 11,955,025 B2
(45) Date of Patent: Apr. 9, 2024

(54) SYSTEMS AND METHODS FOR FACILITATING CREATING OF CUSTOMIZABLE TUTORIALS FOR INSTRUMENTS SPECIFIC TO A PARTICULAR FACILITY

(71) Applicants: Adin Aoki, Union, KY (US); Ethan Aoki, Union, KY (US)

(72) Inventors: Adin Aoki, Union, KY (US); Ethan Aoki, Union, KY (US)

( * ) Notice: Subject to any disclaimer, the term of this patent is extended or adjusted under 35 U.S.C. 154(b) by 0 days.

(21) Appl. No.: 17/993,454

(22) Filed: Nov. 23, 2022

(65) Prior Publication Data

US 2023/0093571 A1 Mar. 23, 2023

Related U.S. Application Data

(63) Continuation-in-part of application No. 16/800,969, filed on Feb. 25, 2020, now abandoned.

(60) Provisional application No. 62/834,755, filed on Apr. 16, 2019.

(51) Int. Cl.
| | |
|---|---|
| *G09B 19/00* | (2006.01) |
| *G09B 5/06* | (2006.01) |
| *G06F 9/451* | (2018.01) |
| *G16H 40/63* | (2018.01) |

(52) U.S. Cl.
CPC ............ *G09B 19/003* (2013.01); *G09B 5/06* (2013.01); *G06F 9/453* (2018.02); *G16H 40/63* (2018.01)

(58) Field of Classification Search
CPC ......... G09B 19/003; G09B 5/06; G06F 9/453; G16H 40/63
See application file for complete search history.

(56) References Cited

U.S. PATENT DOCUMENTS

| | | | |
|---|---|---|---|
| 10,901,762 B1* | 1/2021 | Kuklinski | H04N 21/4788 |
| 2009/0036775 A1* | 2/2009 | Ikuma | A61B 8/5238 |
| | | | 600/443 |
| 2015/0178457 A1* | 6/2015 | Grimley | G06F 3/04817 |
| | | | 705/3 |
| 2015/0213726 A1 | 7/2015 | Holtzman | |
| 2016/0239610 A1* | 8/2016 | Andersen | G16H 10/60 |
| 2017/0202630 A1 | 7/2017 | Gerstner | |
| 2018/0075156 A1* | 3/2018 | Broselow | G06K 7/10861 |
| 2018/0225993 A1 | 8/2018 | Buras | |
| 2018/0369678 A1* | 12/2018 | Yang | A63B 24/0062 |
| 2020/0005949 A1* | 1/2020 | Warkentine | A61B 90/96 |
| 2022/0382442 A1* | 12/2022 | Liang | G06F 3/04845 |

* cited by examiner

*Primary Examiner* — Jack Yip

(57) ABSTRACT

Disclosed herein is a method of facilitating creating of customizable tutorials for instruments specific to a particular facility, in accordance with some embodiments. Accordingly, the method may include a step of receiving, using a communication device, a facility blueprint of a facility from at least one user device. Further, the method may include a step of receiving, using the communication device, an instrument location of an instrument associated with the facility blueprint from the at least one user device. Further, the method may include a step of receiving, using the communication device, a plurality of tutorial information associated with the instrument corresponding to the instrument location from the at least one user device. Further, the method may include a step of storing, using a storage device, the plurality of tutorial information associated with the instrument corresponding to the instrument location.

20 Claims, 23 Drawing Sheets

SYSTEMS AND METHODS FOR FACILITATING CREATING OF CUSTOMIZABLE TUTORIALS FOR INSTRUMENTS SPECIFIC TO A PARTICULAR FACILITY

TECHNICAL FIELD

Generally, the present disclosure relates to the field of data processing. More specifically, the present disclosure relates to systems and methods for facilitating creating of customizable tutorials for instruments specific to a particular facility.

BACKGROUND

Time and money are often wasted due to lack of perfect photographic/auditory memory from training sessions, structured notes, proper planning, time management, proper materials ordered, safety knowledge and clearance, annotated "tricks of the trade", etc. Insufficiently recorded institutional knowledge results in impeded innovation and physical process inefficiencies across every organization or along every individual career. Unclear tutorial documentation limits opportunities to specifically iterate and innovate upon pre-existing tutorials.

Further, current technologies do not allow the user to insert commentary related to the effectiveness of the tutorial. Further, the current technologies do not allow users to upload their own images and videos on how the tutorial can be more precise. Further, the current technologies are not compatible with smartphones and tablets. Further, the current technologies do not allow for tutorials to be mapped along precise locations. Further, the current technologies do not allow for tutorial duration to be recorded. Further, the current technologies do not allow for easy tutorial iteration or innovation to support new process creation. Furthermore, the current technologies do not allow for modification and based on whether the material provides a sufficient explanation and demonstration.

Therefore, there is a need for improved systems and methods for facilitating creating of customizable tutorials for instruments specific to a particular facility that may overcome one or more of the above-mentioned problems and/or limitations.

BRIEF SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method of facilitating creating of customizable tutorials for instruments specific to a particular facility, in accordance with some embodiments. Accordingly, the method may include a step of receiving, using a communication device, a facility blueprint of a facility from at least one user device. Further, the facility blueprint facilitates locating at least one instrument disposed in the facility. Further, the method may include a step of receiving, using the communication device, an instrument location of an instrument associated with the facility blueprint from the at least one user device. Further, the method may include a step of receiving, using the communication device, a plurality of tutorial information associated with the instrument corresponding to the instrument location from the at least one user device. Further, the plurality of tutorial information may include at least one of visual information and aural information. Further, the method may include a step of storing, using a storage device, the plurality of tutorial information associated with the instrument corresponding to the instrument location.

Further disclosed herein is a system for facilitating creating of customizable tutorials for instruments specific to a particular facility, in accordance with some embodiments. Accordingly, the system may include a communication device configured for receiving a facility blueprint of a facility from at least one user device. Further, the facility blueprint facilitates locating at least one instrument disposed in the facility. Further, the communication device may be configured for receiving an instrument location of an instrument associated with the facility blueprint from the at least one user device. Further, the communication device may be configured for receiving a plurality of tutorial information associated with the instrument corresponding to the instrument location from the at least one user device. Further, the plurality of tutorial information may include at least one of visual information and aural information. Further, the system may include a storage device configured for storing the plurality of tutorial information associated with the instrument corresponding to the instrument location.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
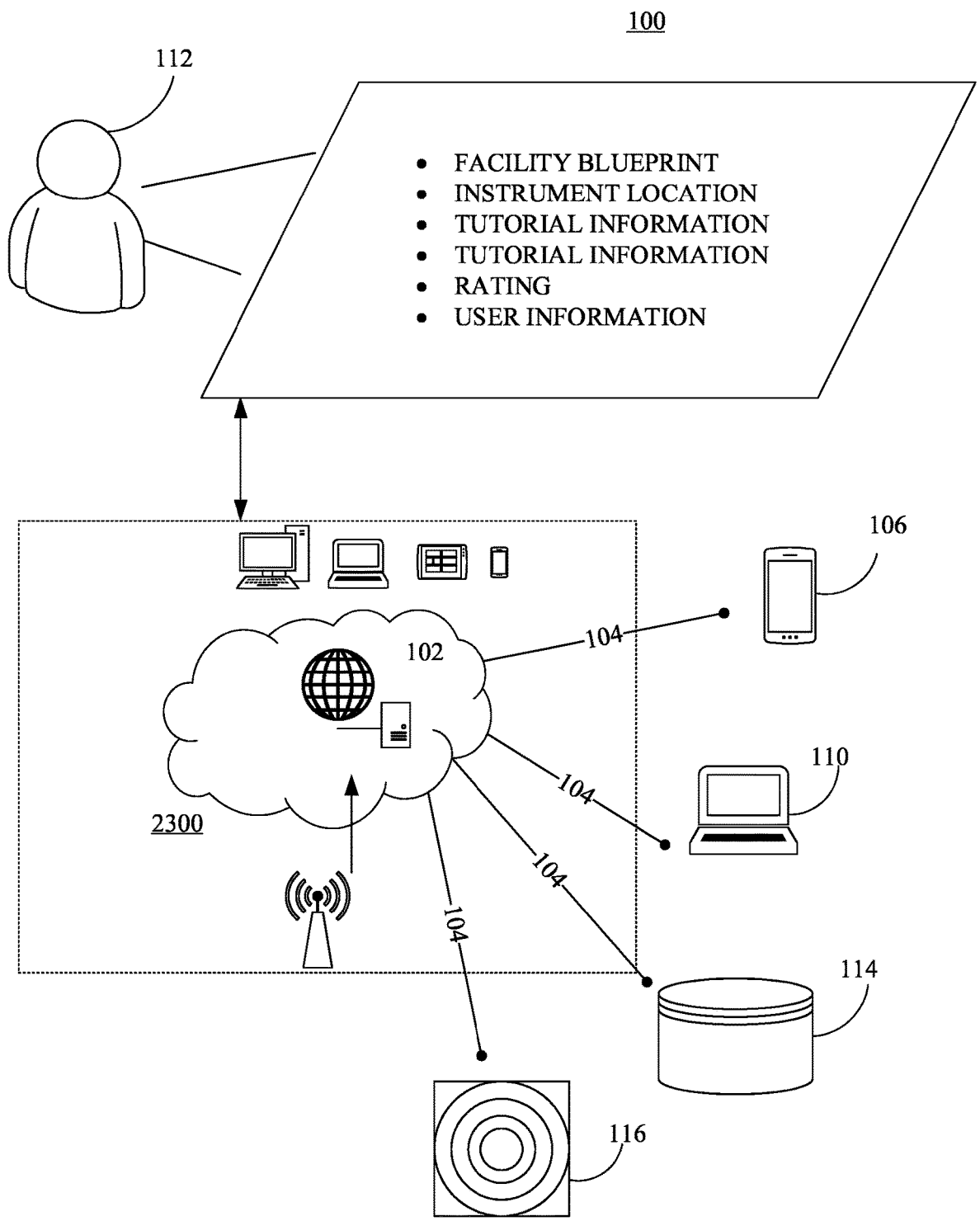
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of systems and methods for facilitating creating of customizable tutorials for instruments specific to a particular facility, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes systems and methods for facilitating creating of customizable tutorials for instruments specific to a particular facility. Further, the disclosed system may be associated with a software application "Inscriptures" that allows users to use and create customizable tutorials that are specific to a particular environment. Users can upload images, videos, and audio to create a comprehensive tutorial on how to achieve a certain goal. Since laboratory researchers are often busy and unable to provide individual supervision, it is helpful for students and laboratory workers to have continuous access to information on how to use laboratory equipment. The disclosed system provides a step-by-step interactive and customizable tutorial on how to use equipment and materials that are found in a laboratory.

Further, the disclosed system may include an unprecedented platform by which multimedia can automatically be structured into a step by step pictorial tool navigating users on how to safely use the materials around them to yield the products or results intended. The customizable visibility of the platform provides unprecedented accountability in method-dependent environments where coworkers or risk management workers may correct, or update needed safety information.

Further, to use the software application Inscriptures, the user may first open the application and draw the blueprint for the laboratory area with which the tutorials will correspond. More likely than not, the laboratory will feature a number of instruments, each of which may have an accompanying tutorial. Thus, a blueprint of the environment allows a user to go directly to an area of the laboratory and input information regarding a specific instrument in that area. To enter instructional information into the software application, there are three steps. First, the user takes a photo of each step that shows how to use a specific laboratory instrument and enters the duration of each step. Second, the software application will prompt users to input the preferred material-specific vendors and any safety information associated with using the instrument at each step in the tutorial. Third, the user is able to select images and relocate them within the laboratory blueprint so that the tutorial appears in the same location as where the equipment appears in the actual laboratory. The disclosed system may be expanded to different industries. Further, the software application Inscriptures may provide instant instructional photographs and explanations on how to use laboratory equipment. Such instructions are normally provided by laboratory instructors, however, the Inscriptures fills the void when instructors are not present. Further, the software application Inscriptures allows users to upload and store existing tutorials that can be accessed remotely and at a later time.

Further, the software application Inscriptures may prompt the user to draw or insert a blueprint of the laboratory such that each piece of equipment physically present in the laboratory will be reflected on the blueprint. Further, the software application Inscriptures may allow the user to select, on the blueprint, a specific piece of equipment within the laboratory. Further, the software application Inscriptures may take instructional photographs that provide a step-by-step description of how to use the equipment. Further, the software application Inscriptures may amend to each photograph a description of the action that is executed in the photograph, the duration of the action, and the materials that are necessary for each step. Further, the software application Inscriptures may allow the user to attach the completed tutorial to the respective piece of equipment on the blueprint. Further, the software application Inscriptures may allow future users to interact with each piece of equipment's tutorial such that the user will understand how to use the equipment without having to work under the supervision of an experienced scientist.

Further, the software application Inscriptures organizes all recorded photos into an editable succession of steps. Further, the software application Inscriptures facilitates personalized navigation of reason through time, material, and space.

Further, for navigating time, every aforementioned picture later prompts that the user enters an action with completion time, for example, "Insert suture—30 seconds". Further, navigating through the time may include pairing the photo with the bolded word into a swipe able timeline. Further, for navigating material, the software application Inscriptures asks that users input preferred material-specific venders and associated safety information, for example, "SuturesSupply.com—PDF on Soluble vs. Insoluble Sutures". Further, the software application Inscriptures may enrich protocols with cautionary and acquisitional knowledge. Further, for navigating space, the software application Inscriptures' photographic foundation already upholds the visual. Further, each photo of the visual is capable of being replaced to suite the appropriate environment, for example, "New Surgery Table? Keep the words, replace the photo". Further, the software application Inscriptures may facilitate enriching the navigation through the space. Further, the software application Inscriptures may allow the user to upload and pin steps to floorplans, a materials-storage/disposal locator, and finally exportable QR code labels that inexpensively link the above digital world to the environmental world, turning smartphones into exploratory or referential scanners.

Further, the disclosed system may be adapted into alternative smartphone applications, each catered to a particular industry's user bases. Further, the user bases fall into or append three archetypes. Further, the three archetypes may include users, suppliers, and risk managers.

Further, the disclosed system may be employed in assays, for the biomedical field, which is research-centric. Further, the disclosed system may allow the users to hyperlink to relevant journal articles. Further, the disclosed system may allow the suppliers to advertise their relevant products in-app. Further, the disclosed system may allow animal or human-associated risk management teams, such as Institutional Animal Care and Use Committee (IACUC) or Institutional Review Board (IRB), to comment or request an animal/patient image be blurred for privacy issues. Finally, publications such as Cell would be able to consolidate their method section into a simple QR code and manufacturers could also package pre-prepared QR codes assays with their devices or equipment.

Further, the disclosed system may be employed in engineering field for infrastructures that is research-centric, however with minute changes to better suite engineers. An example includes a built-in calculator and ruler for the users.

Further, the disclosed system may be employed in chemixtures for the chemistry field which is research-centric, however with minute changes to better suite chemists. An example includes chemical Safety Data Sheets for both users and risk managers.

Further, the disclosed system may be employed in houscripts for the property management industry which is household-centric, allowing users to convey "fix-it-yourself" guides, utility or house-machine suppliers to send operational stickers, and landlords or public assessors to oversee household changes.

Further, the disclosed system may be employed in manufixtures for the manufacturing industry which is factory-centric, allowing the users to synchronize machine output patterns with app navigation, notification for machine parts suppliers of any machine operational concern, and factory inspectors a provided log of app use and also reported employees trained.

Referring now to figures, FIG. 1 is an illustration of an online platform 100 consistent with various embodiments of the present disclosure. By way of non-limiting example, the online platform 100 to facilitate creating of customizable tutorials for instruments specific to a particular facility may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, and sensors 116 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 2300.

The present invention may utilize a Web-based graphical user interface (GUI). Any web-based development platform, such as the Microsoft Windows Distributed Internet Architecture (WINDNA), may be used to build and deploy the web-based GUI. In other words, the GUI applications may be hosted by an Internet information server (IIS), such as the Microsoft IIS, and utilize a teleprocessing or transaction processing monitor (TP monitor); such as the Microsoft Transaction Server (MTS) to provide the web-based GUI and its website(s). The deployment of the web-based GUI of the present invention also includes server site replication to ensure that the server farms contain identical applications and information.

Figure 2:
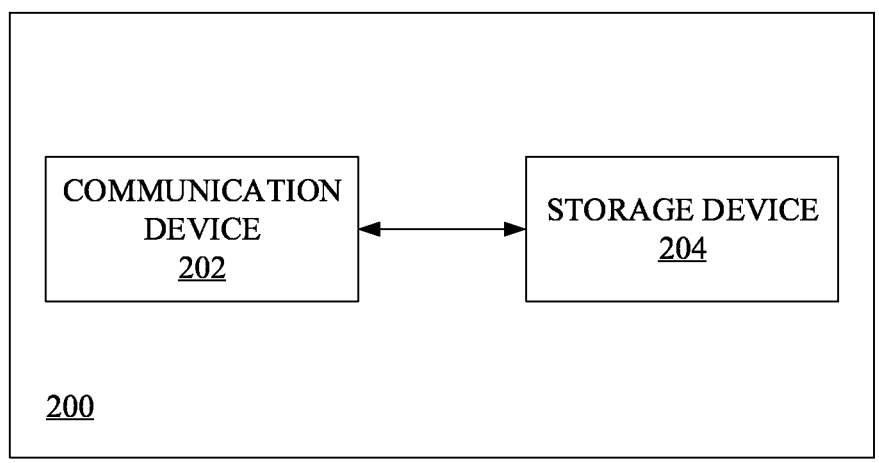
FIG. 2 is a block diagram of a system for facilitating creating of customizable tutorials for instruments specific to a particular facility, in accordance with some embodiments.

FIG. 2 is a block diagram of a system 200 for facilitating creating of customizable tutorials for instruments specific to a particular facility, in accordance with some embodiments. Accordingly, the system may include a communication device 202 and a storage device 204.

Further, the communication device 202 may be configured for receiving a facility blueprint of a facility from at least one user device. Further, the facility blueprint facilitates locating at least one instrument disposed in the facility. Further, the communication device 202 may be configured for receiving an instrument location of an instrument associated with the facility blueprint from the at least one user device. Further, the communication device 202 may be configured for receiving a plurality of tutorial information associated with the instrument corresponding to the instrument location from the at least one user device. Further, the plurality of tutorial information may include at least one of visual information and aural information.

Further, the storage device 204 may be configured for storing the plurality of tutorial information associated with the instrument corresponding to the instrument location.

Further, in some embodiments, the communication device 202 may be configured for transmitting the facility blueprint to at least one first user device. Further, the communication device 202 may be configured for receiving an instrument indication corresponding to an instrument of the at least one instrument from the at least one first user device. Further, the communication device 202 may be configured for transmitting a plurality of tutorial information associated with the instrument to the at least one first user device. Further, the at least one first user device may be configured for presenting the plurality of tutorial information. Further, the storage device 204 may be configured for retrieving the plurality of tutorial information associated with the instrument based on the instrument indication.

The user device (including the at least one first user device) of the present invention may include various types of portable apparatuses having a display function, such as a mobile phone, a smartphone, a portable multimedia player (PMP), a personal digital assistant (PDA), a tablet PC, and a navigation system.

Figure 3:
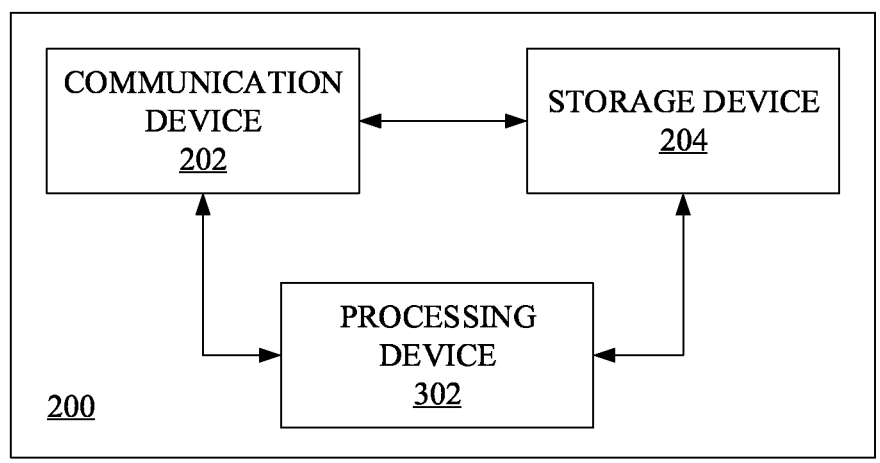
FIG. 3 is a block diagram of the system for facilitating creating of customizable tutorials for instruments specific to a particular facility, in accordance with some embodiments.

In further embodiments, the system may include a processing device 302 (as shown in FIG. 3) communicatively coupled with the communication device 202 and the storage device 204. Further, the communication device 202 may be configured for receiving at least one user information from the at least one user device. Further, the processing device 302 may be configured for analyzing the plurality of tutorial information based on the at least one user information. Further, the processing device 302 may be configured for generating a plurality of new tutorial information corresponding to the plurality of tutorial information based on the analyzing. Further, the storage device 204 may be configured for storing the plurality of new tutorial information associated with the instrument corresponding to the instrument location.

Further, in some embodiments, the at least one user device may be configured for generating the plurality of tutorial information.

In further embodiments, the communication device 202 may be configured for receiving at least one feedback associated with the plurality of tutorial information from the at least one user device. Further, the communication device 202 may be configured for transmitting a rating to the at least one user device. Further, the processing device 302 may be configured for analyzing the at least one feedback. Further, the processing device 302 may be configured for generating the rating for the plurality of tutorial information based on the analyzing.

In further embodiments, the communication device 202 may be configured for receiving an instrument location request associated with the instrument from the at least one user device. Further, the processing device 302 may be configured for analyzing the instrument location request. Further, the processing device 302 may be configured for determining a new instrument location of the instrument associated with the facility blueprint based on the analyzing. Further, the storage device 204 may be configured for storing the plurality of tutorial information associated with the instrument corresponding to the new instrument location.

In further embodiments, the processing device 302 may be configured for identifying a plurality of tutorial metadata associated with the plurality of tutorial information. Further, the processing device 302 may be configured for analyzing the plurality of tutorial information based on the plurality of tutorial metadata. Further, the storage device 204 may be configured for storing the plurality of tutorial information associated with the instrument corresponding to the instrument location based on the analyzing.

In further embodiments, the communication device 202 may be configured for receiving a plurality of instrument information associated with the instrument from the at least one user device. Further, the communication device 202 may be configured for receiving a plurality of additional information corresponding to the plurality of instrument information from the at least one user device. Further, the processing device 302 may be configured for analyzing the plurality of instrument information and the plurality of additional information. Further, the processing device 302 may be configured for generating the plurality of tutorial information based on the analyzing.

Further, in some embodiments, the plurality of tutorial information may be characterized by at least one tutorial characteristic. Further, the at least one tutorial characteristic may include at least one of a description, an instruction, and a duration.

In further embodiments, the communication device 202 may be configured for receiving at least one sensor data from at least one sensor. Further, the at least one sensor may be configured for generating the at least one sensor data associated with the at least one instrument. Further, the communication device 202 may be configured for transmitting a plurality of tutorial information to the at least one user device. Further, the processing device 302 may be configured for analyzing the at least one sensor data. Further, the processing device 302 may be configured for identifying an instrument of the at least one instrument based on the analyzing. Further, the storage device 204 may be configured for retrieving the plurality of tutorial information based on the identifying.

FIG. 3 is a block diagram of the system 200 for facilitating creating of customizable tutorials for instruments specific to a particular facility, in accordance with some embodiments. Accordingly, the system 200 further comprises the processing device 302.

Figure 4:
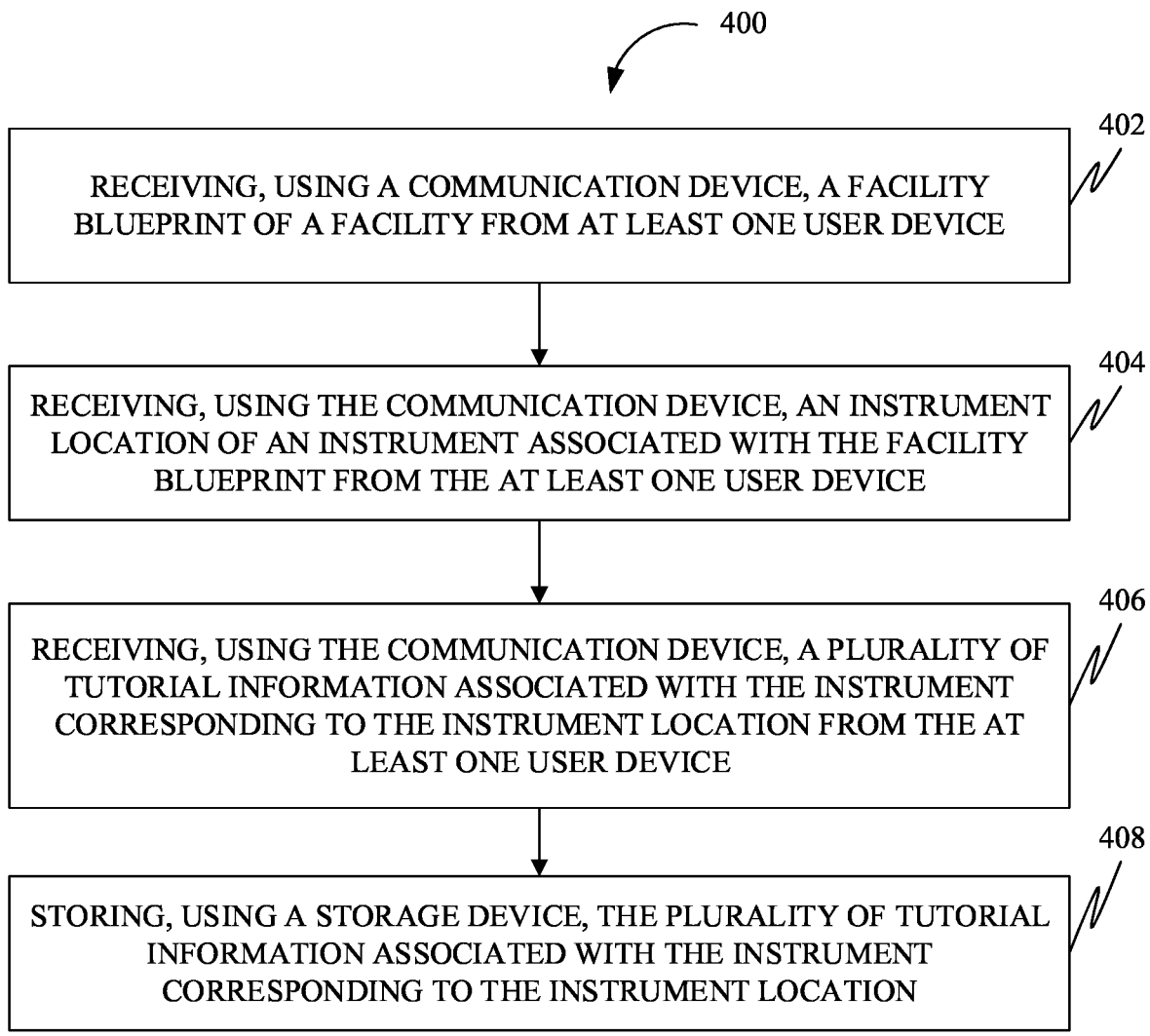
FIG. 4 is a flowchart of a method for facilitating creating of customizable tutorials for instruments specific to a particular facility, in accordance with some embodiments.

FIG. 4 is a flowchart of a method 400 for facilitating creating of customizable tutorials for instruments specific to a particular facility, in accordance with some embodiments.

Accordingly, at 402, the method 400 may include a step of receiving, using a communication device, a facility blueprint of a facility from at least one user device. Further, the facility blueprint facilitates locating at least one instrument disposed in the facility.

In some embodiments, the method 400 may provide a screen on the user device to receive the facility blueprint, the screen can be any suitable screen associated with a computing device, such as a computer or mobile device such as a phone or tablet. The screen may prompt a user to enter a selection of one of facility blueprint input methods that can be either a drawing method which allows the user to draw the facility blueprint and an inserting method which allows the user to insert the facility blueprint to the user device or a device connected to the user device for such purposes. The user device may configured or include a mechanism for user to insert the facility blueprint to the user device or the user device may be connected to a device that facilitates the inserting of the facility blueprint to the device and transmit the inserted facility blueprint to the present invention. Such device that facilitates the inserting of the facility blueprint may include a scanner.

In such embodiments, the method 400 may include steps of: providing a screen for capturing tutorial information, wherein the screen includes a list of facility blueprint input methods, vendors (for facilities or instruments), and safety information associated with using at least one instrument;
  prompting entry of a selection of one of the facility blueprint input methods and vendors, wherein the facility blueprint input methods include a drawing method and an inserting method;
  accepting, at the screen, entry of a selected method and a selected vendor;

providing a screen on at least one user device for drawing the facility blueprint and accepting, at the screen, entry of a drawn facility blueprint if the selected method is the drawing method;

providing a screen on the at least one user device for inserting the facility blueprint and accepting, at the screen, entry of an inserted facility blueprint if the selected method is the inserting method;

receiving the facility blueprint from at least one user device, wherein the facility blueprint facilitates locating at least one instrument disposed in the facility, wherein the facility blueprint includes at least one relocatable instrument image.

Further, at 404, the method 400 may include a step of receiving, using the communication device, an instrument location of an instrument associated with the facility blueprint from the at least one user device.

In some embodiments, the method 400 may allow the user to adjust one or more instrument locations by comparing the actual (current) instrument location with the location of the instrument shown on the facility blueprint received and relocating the relocatable instrument images on the facility blueprint that may be displayed on the user device. In such embodiments, the method 400 may include steps of: taking a photo of each step of a plurality of tutorial information that may show how to use a specific instrument and entering a duration of each step; displaying the photo on the at least one user device.

For comparison, the method 400 may include a step of receiving an actual instrument location of an instrument associated with the facility blueprint from the at least one user device;

providing a screen for user to select the at least one instrument image and relocate the at least one instrument image within the facility blueprint so that the at least one instrument image appears on the actual instrument location in the facility blueprint.

Further, at 406, the method 400 may include a step of receiving, using the communication device, a plurality of tutorial information associated with the instrument corresponding to the instrument location from the at least one user device. Further, the plurality of tutorial information may include at least one of visual information and aural information. Further, in an embodiment, the at least one user device may be configured for generating the plurality of tutorial information. Further, the plurality of tutorial information may be characterized by at least one tutorial characteristic. Further, the at least one tutorial characteristic may include at least one of a description, an instruction, and a duration.

In some embodiments, the method 400 may include following steps to receive and create the plurality of tutorial information. The methods 400 may include steps of: capturing, by using a camera or microphone, a timestamp, at least one visual or aural information to create a plurality of tutorial information, creating a plurality of tutorial information based on the visual or aural information and the timestamp by using at least one user device configured to receive the actual instrument location from a GPS receiver (which may be included in the user device) and associate the actual instrument location with the visual or aural information and timestamp, providing a sequential information of the plurality of tutorial information, by using the at least one user device that tracks time and the actual instrument location information from the GPS receiver.

Further, at 408, the method 400 may include a step of storing, using a storage device, the plurality of tutorial information associated with the instrument corresponding to the instrument location.

Figure 5:
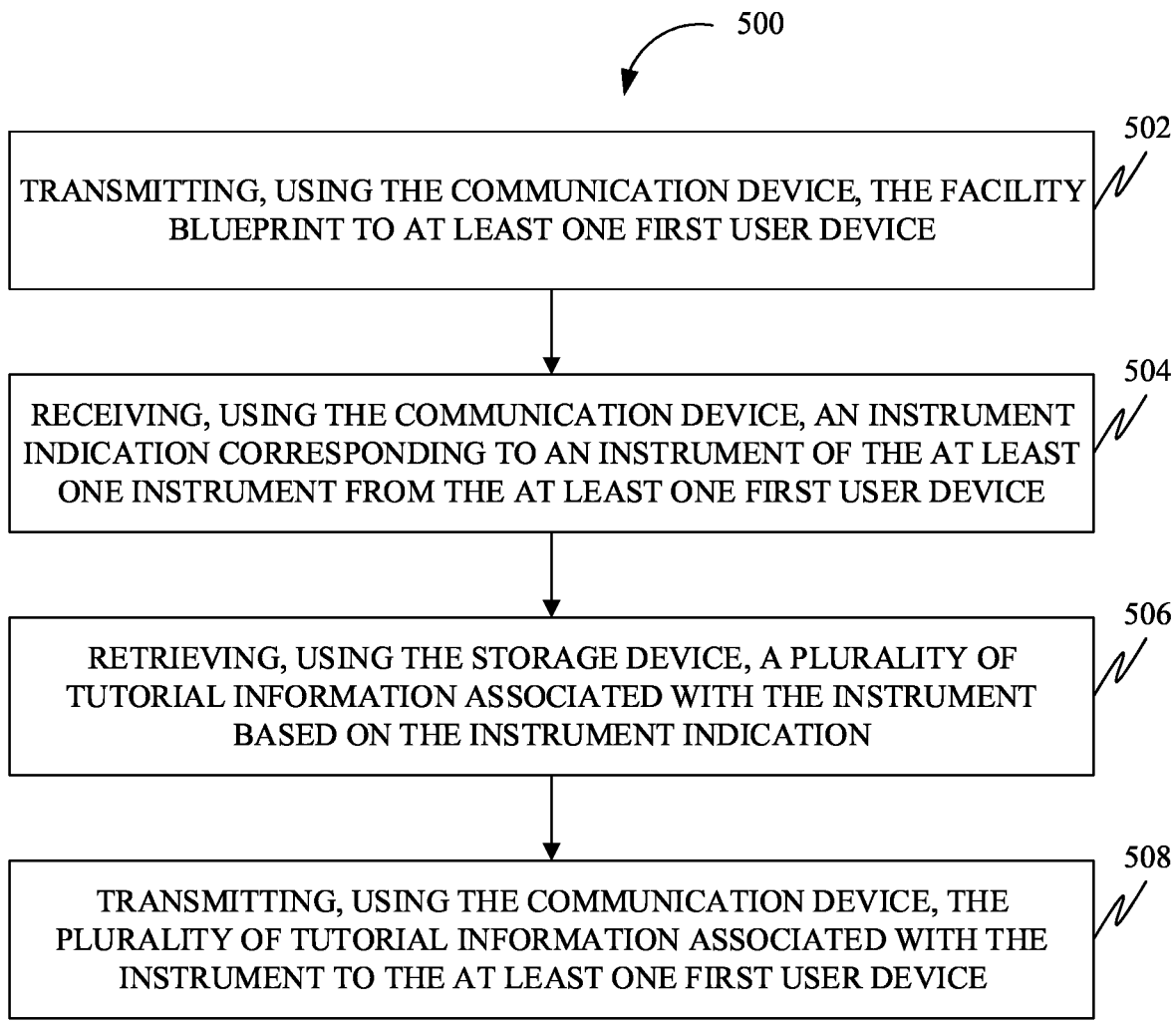
FIG. 5 is a flowchart of a method for facilitating retrieving of tutorial information associated with an instrument, in accordance with some embodiments.

FIG. 5 is a flowchart of a method 500 for facilitating retrieving of tutorial information associated with an instrument, in accordance with some embodiments. Accordingly, at 502, the method 500 may include a step of transmitting, using the communication device, the facility blueprint to at least one first user device.

Further, at 504, the method 500 may include a step of receiving, using the communication device, an instrument indication corresponding to an instrument of the at least one instrument from the at least one first user device.

Further, at 506, the method 500 may include a step of retrieving, using the storage device, a plurality of tutorial information associated with the instrument based on the instrument indication.

Further, at 508, the method 500 may include a step of transmitting, using the communication device, the plurality of tutorial information associated with the instrument to the at least one first user device. Further, the at least one first user device may be configured for presenting the plurality of tutorial information.

Figure 6:
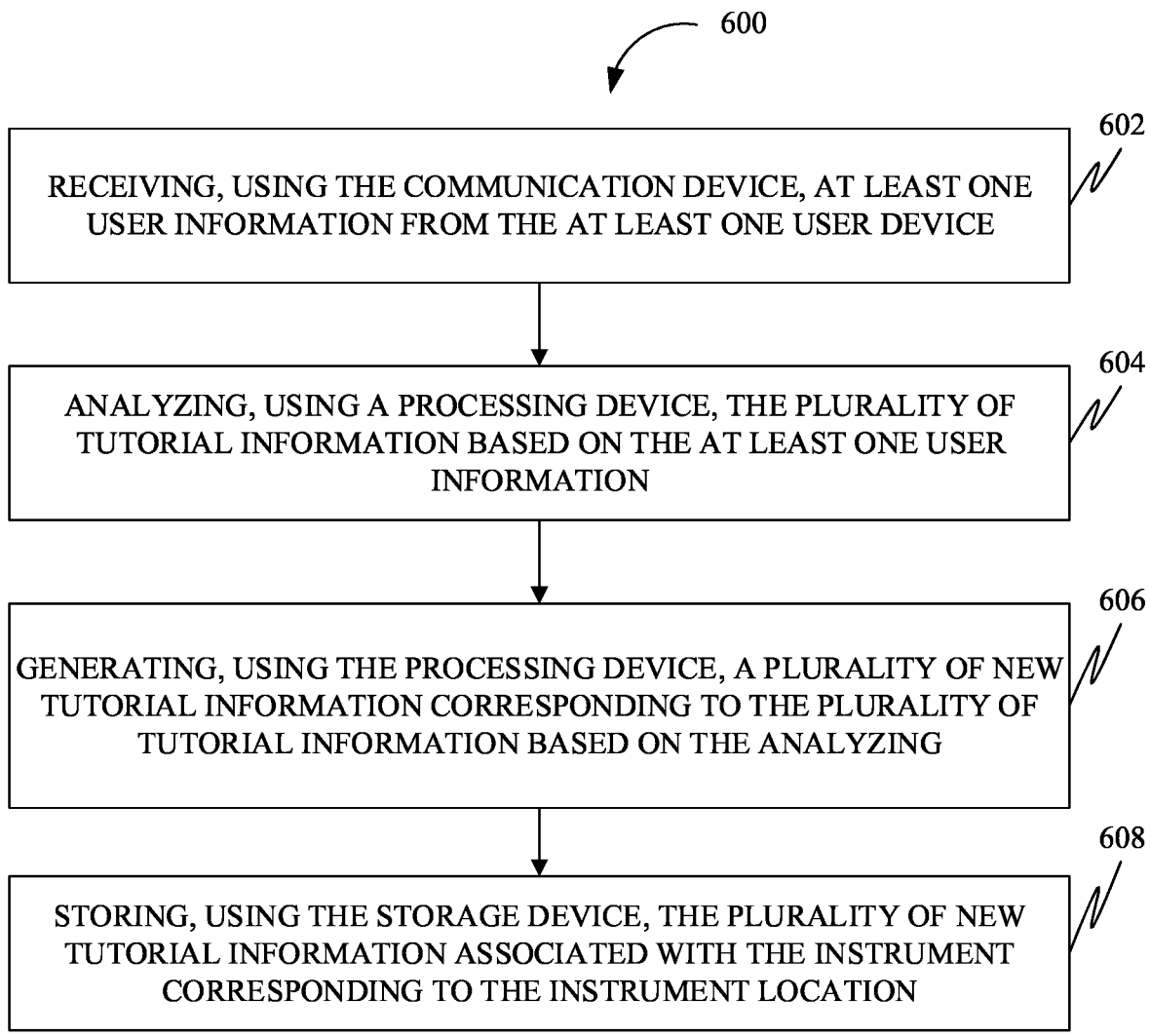
FIG. 6 is a flowchart of a method for facilitating generation of new tutorial information based on user information, in accordance with some embodiments.

FIG. 6 is a flowchart of a method 600 for facilitating the generation of new tutorial information based on user information, in accordance with some embodiments. Accordingly, at 602, the method 600 may include a step of receiving, using the communication device, at least one user information from the at least one user device.

Further, at 604, the method 500 may include a step of analyzing, using a processing device, the plurality of tutorial information based on the at least one user information.

Further, at 606, the method 600 may include a step of generating, using the processing device, a plurality of new tutorial information corresponding to the plurality of tutorial information based on the analyzing.

Further, at 608, the method 600 may include a step of storing, using the storage device, the plurality of new tutorial information associated with the instrument corresponding to the instrument location.

Figure 7:
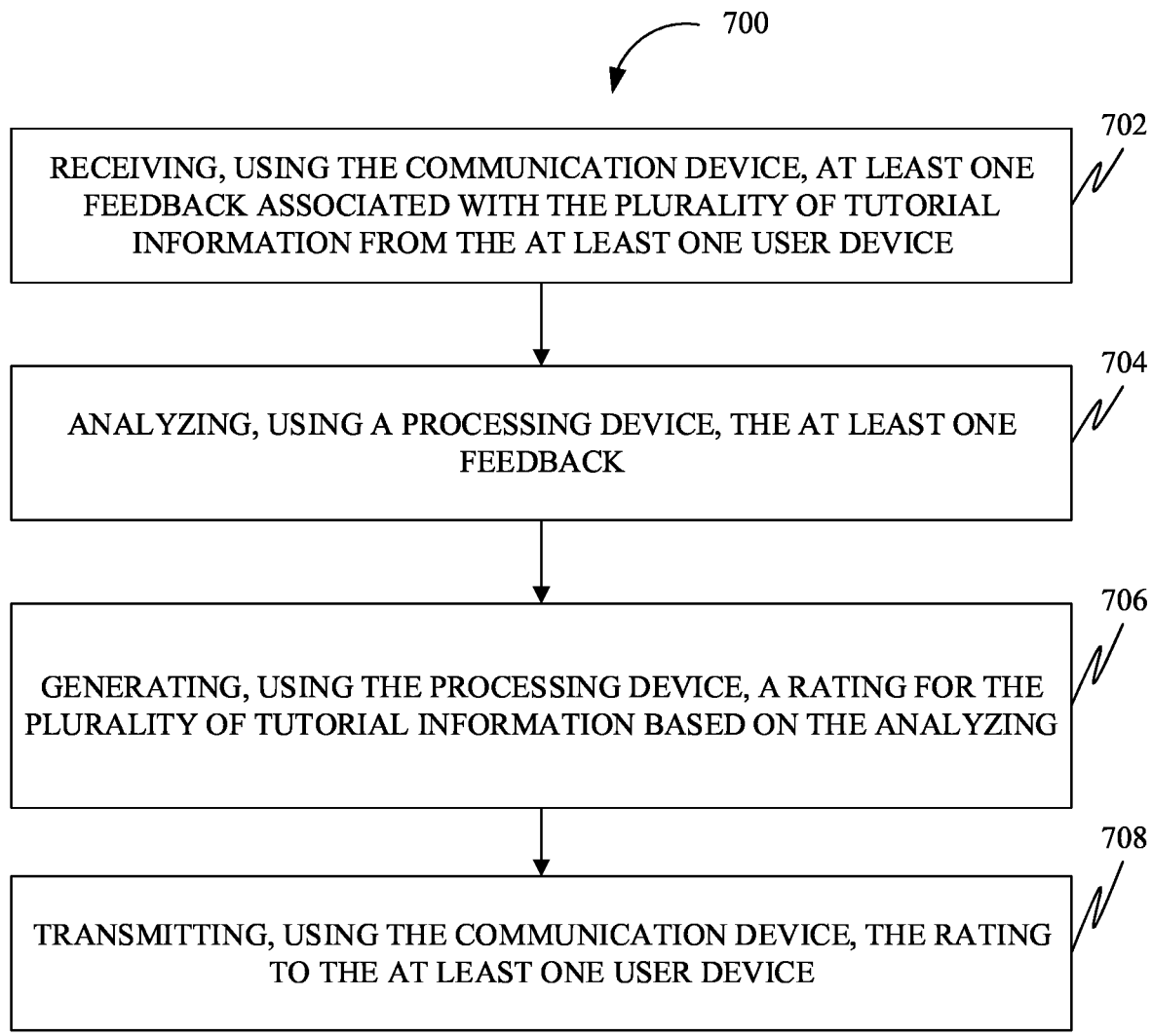
FIG. 7 is a flowchart of a method for facilitating generation of rating associated with tutorial information, in accordance with some embodiments.

FIG. 7 is a flowchart of a method 700 for facilitating generation of rating associated with tutorial information, in accordance with some embodiments. Accordingly, at 702, the method 700 may include a step of receiving, using the communication device, at least one feedback associated with the plurality of tutorial information from the at least one user device.

Further, at 704, the method 700 may include a step of analyzing, using a processing device, the at least one feedback.

Further, at 706, the method 700 may include a step of generating, using the processing device, a rating for the plurality of tutorial information based on the analyzing.

Further, at 708, the method 700 may include a step of transmitting, using the communication device, the rating to the at least one user device.

Figure 8:
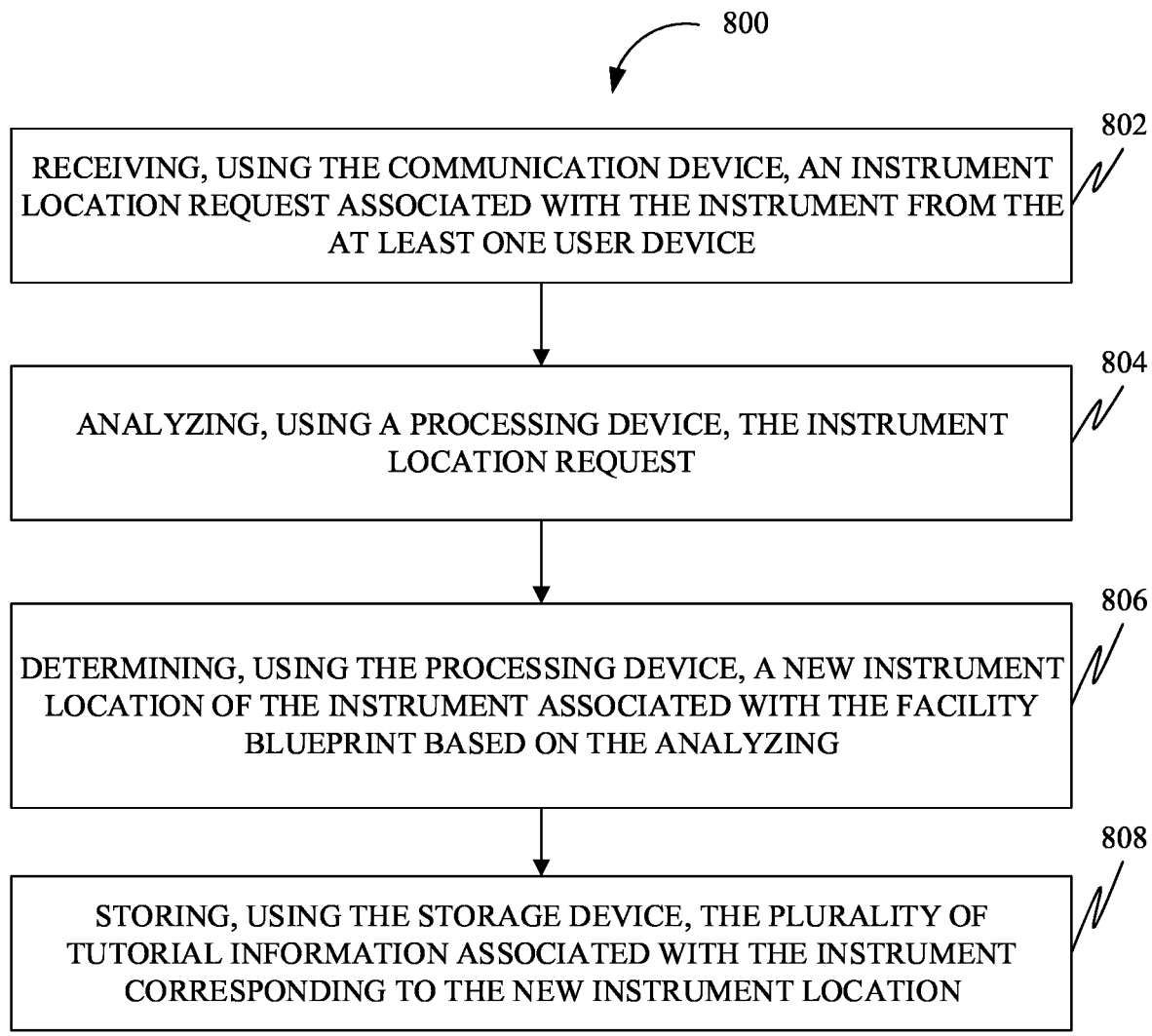
FIG. 8 is a flowchart of a method for facilitating determining of a new instrument location based on instrument location request, in accordance with some embodiments.

FIG. 8 is a flowchart of a method 800 for facilitating determining of a new instrument location based on instrument location request, in accordance with some embodiments. Accordingly, at 802, the method 800 may include a step of receiving, using the communication device, an instrument location request associated with the instrument from the at least one user device.

Further, at 804, the method 800 may include a step of analyzing, using a processing device, the instrument location request.

Further, at 806, the method 800 may include a step of determining, using the processing device, a new instrument location of the instrument associated with the facility blueprint based on the analyzing.

Further, at 808, the method 800 may include a step of storing, using the storage device, the plurality of tutorial information associated with the instrument corresponding to the new instrument location.

Figure 9:
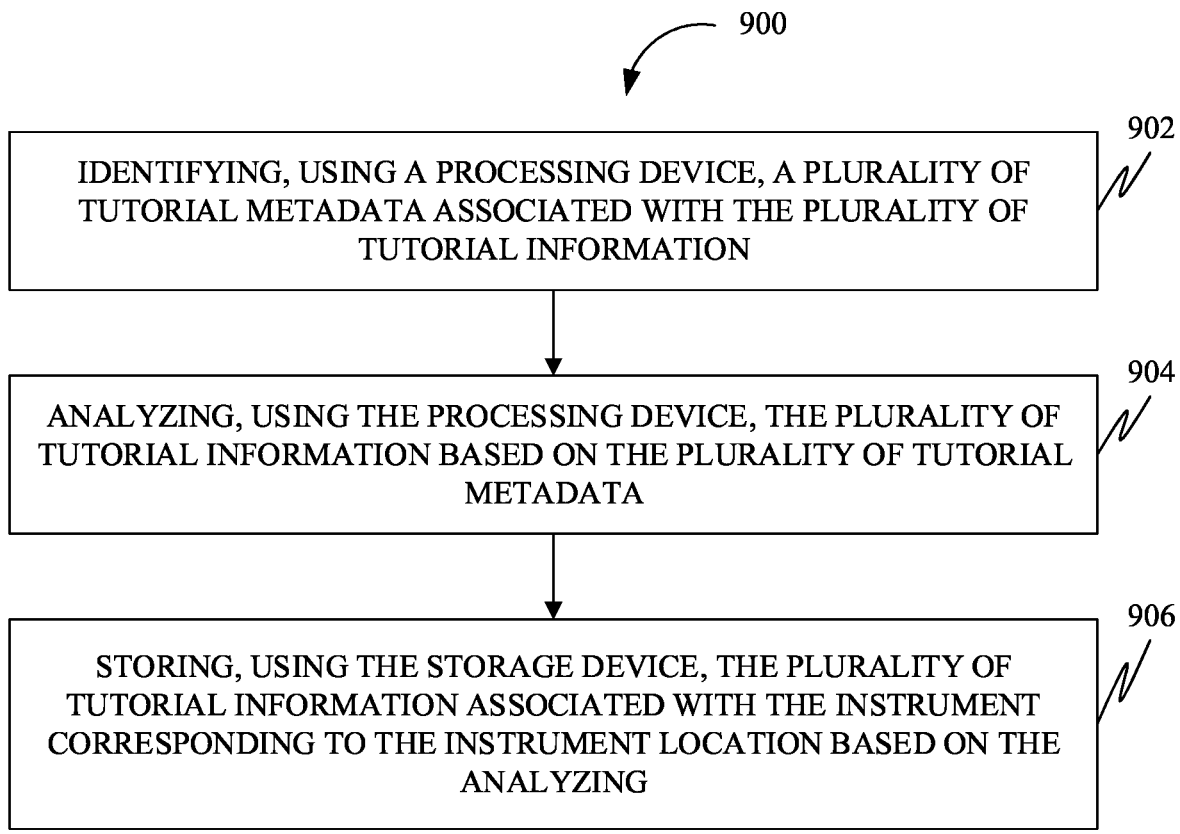
FIG. 9 is a flowchart of a method for facilitating identifying a tutorial metadata associated with tutorial information, in accordance with some embodiments.

FIG. 9 is a flowchart of a method 900 for facilitating identifying a tutorial metadata associated with tutorial information, in accordance with some embodiments. Accordingly, at 902, the method 900 may include a step of identifying, using a processing device, a plurality of tutorial metadata associated with the plurality of tutorial information.

Further, at 904, the method 900 may include a step of analyzing, using the processing device, the plurality of tutorial information based on the plurality of tutorial metadata.

Further, at 906, the method 900 may include a step of storing, using the storage device, the plurality of tutorial information associated with the instrument corresponding to the instrument location based on the analyzing.

Figure 10:
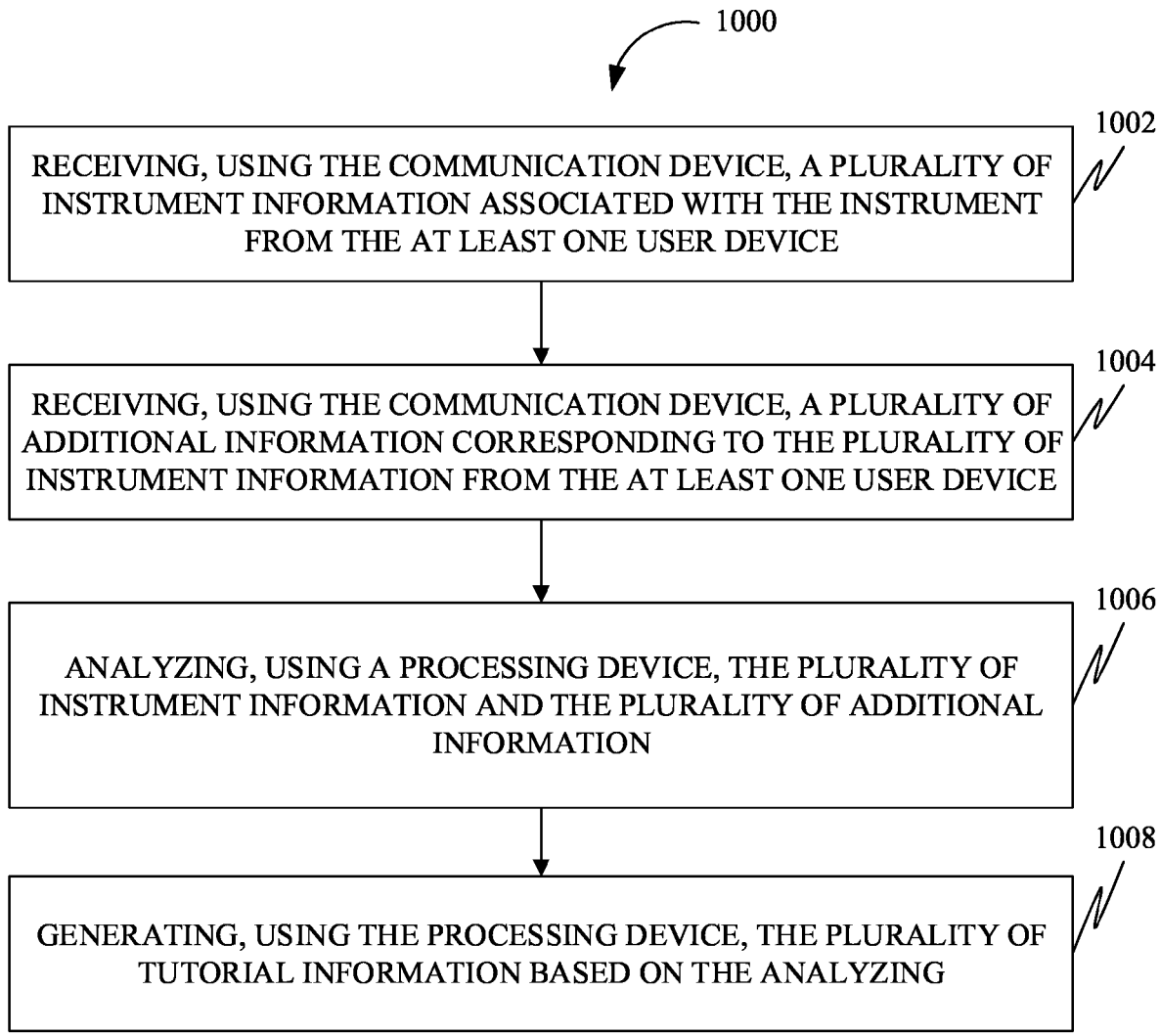
FIG. 10 is a flowchart of a method for generating tutorial information based on additional information, in accordance with some embodiments.

FIG. 10 is a flowchart of a method 1000 for generating tutorial information based on additional information, in accordance with some embodiments. Accordingly, at 1002, the method 1000 may include a step of receiving, using the communication device, a plurality of instrument information associated with the instrument from the at least one user device.

Further, at 1004, the method 1000 may include a step of receiving, using the communication device, a plurality of additional information corresponding to the plurality of instrument information from the at least one user device.

Further, at 1006, the method 1000 may include a step of analyzing, using a processing device, the plurality of instrument information and the plurality of additional information.

Further, at 1008, the method 1000 may include a step of generating, using the processing device, the plurality of tutorial information based on the analyzing.

Figure 11:
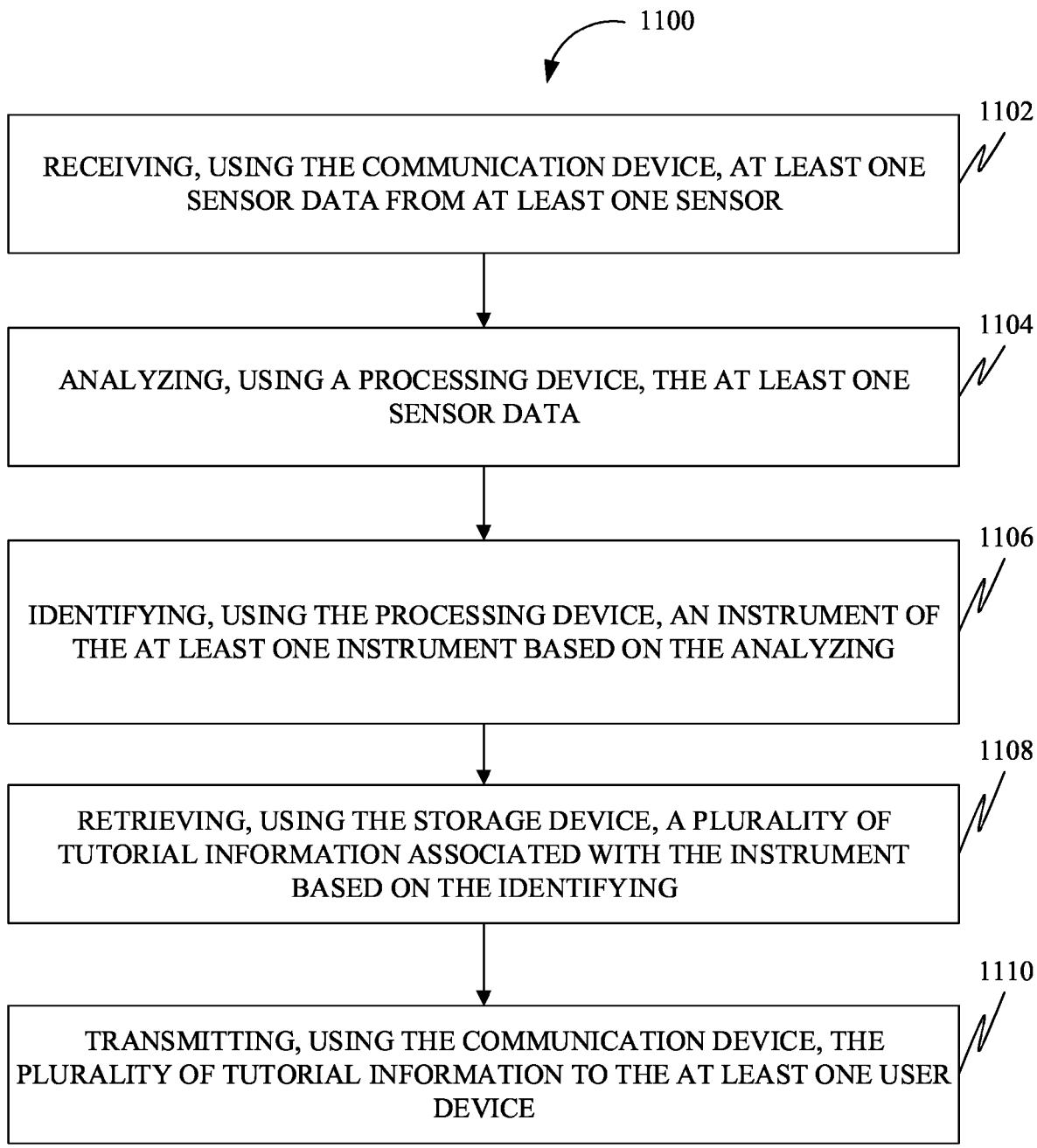
FIG. 11 is a flowchart of a method for facilitating retrieving of tutorial information associated with an instrument based on sensor data, in accordance with some embodiments.

FIG. 11 is a flowchart of a method 1100 for facilitating retrieving of tutorial information associated with an instrument based on a sensor data, in accordance with some embodiments. Accordingly, at 1102, the method 1100 may include a step of receiving, using the communication device, at least one sensor data from at least one sensor. Further, the at least one sensor may be configured for generating the at least one sensor data associated with the at least one instrument.

Further, at 1104, the method 1100 may include a step of analyzing, using a processing device, the at least one sensor data.

Further, at 1106, the method 1100 may include a step of identifying, using the processing device, an instrument of the at least one instrument based on the analyzing.

Further, at 1108, the method 1100 may include a step of retrieving, using the storage device, a plurality of tutorial information associated with the instrument based on the identifying.

Further, at 1110, the method 1100 may include a step of transmitting, using the communication device, the plurality of tutorial information to the at least one user device.

Figure 12:
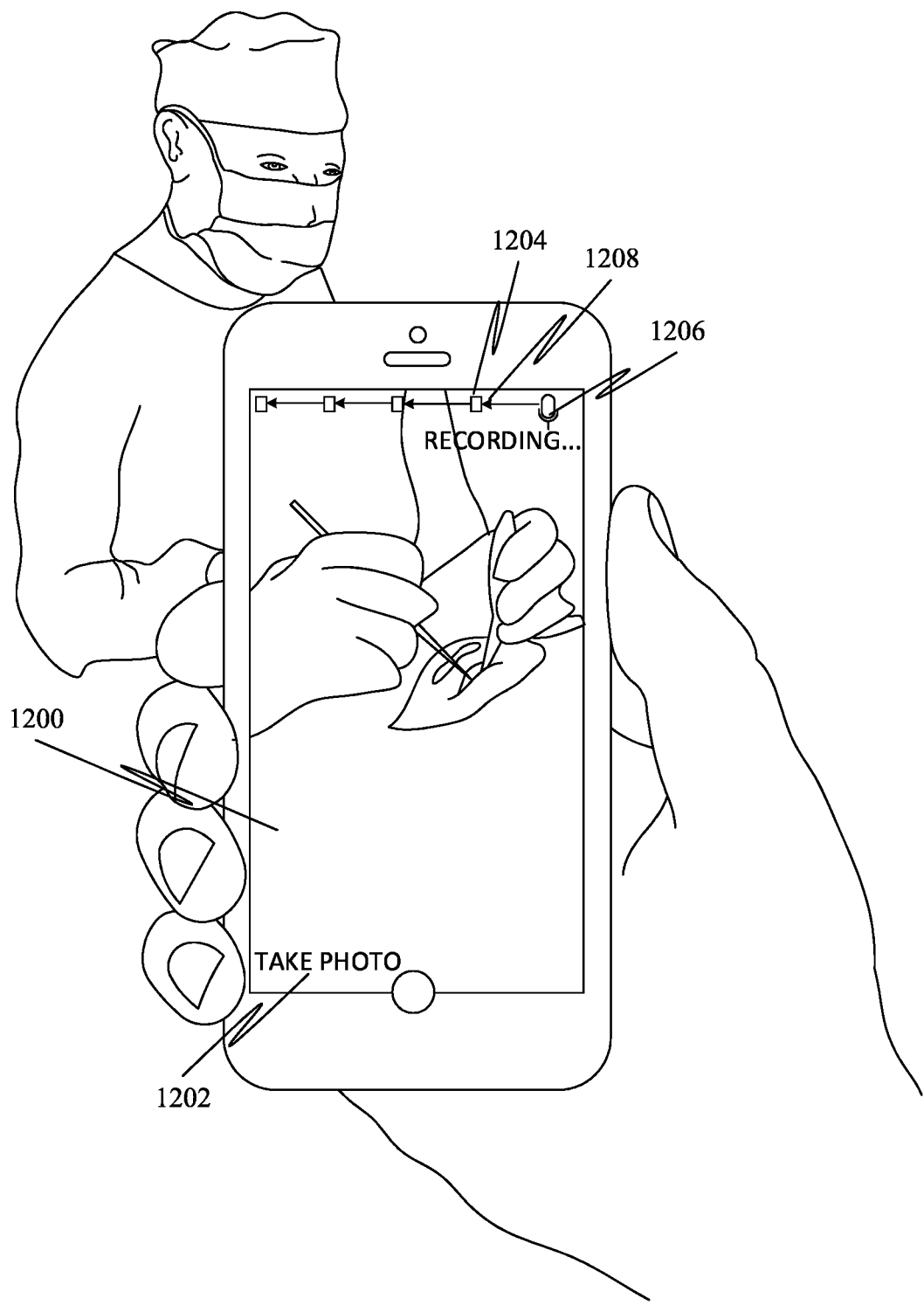
FIG. 12 is a screenshot of a user interface associated with a software application, in accordance with some embodiments.

FIG. 12 is a screenshot of a user interface 1200 associated with a software application, in accordance with some embodiments. Accordingly, upon opening the software application by a user, a screen of smartphone functions as a visualization 1202 of each step. Further, the visualization 1202 may include a visual capture of step. Further, a section 1204 of the user interface 1200, as the user captures images for the tutorial, each image is timestamped and is organized in linear succession. Further, the section 1204 may illustrate captured steps now timestamped and organized according to a linear succession of time. Further, the user can capture audio that may accompany any step in the tutorial by pressing a microphone 1206 on the user interface 1200. Further, a section 1208 may facilitate reviewing of the linear succession of the tutorial's audio by the user. Further, the user interface 1200 may depict the successive stepwise capture of a demonstrated method using a device capable of audiovisual recording, such as a smartphone. Further, the capture results in the creation of a novel audiovisual file type capable of timestamping audio a string of audio with timestamped visual recordings, photos or short videos as selected by the viewer. Further, the microphone 1206 may facilitate audial capture of the demonstration.

Figure 13:
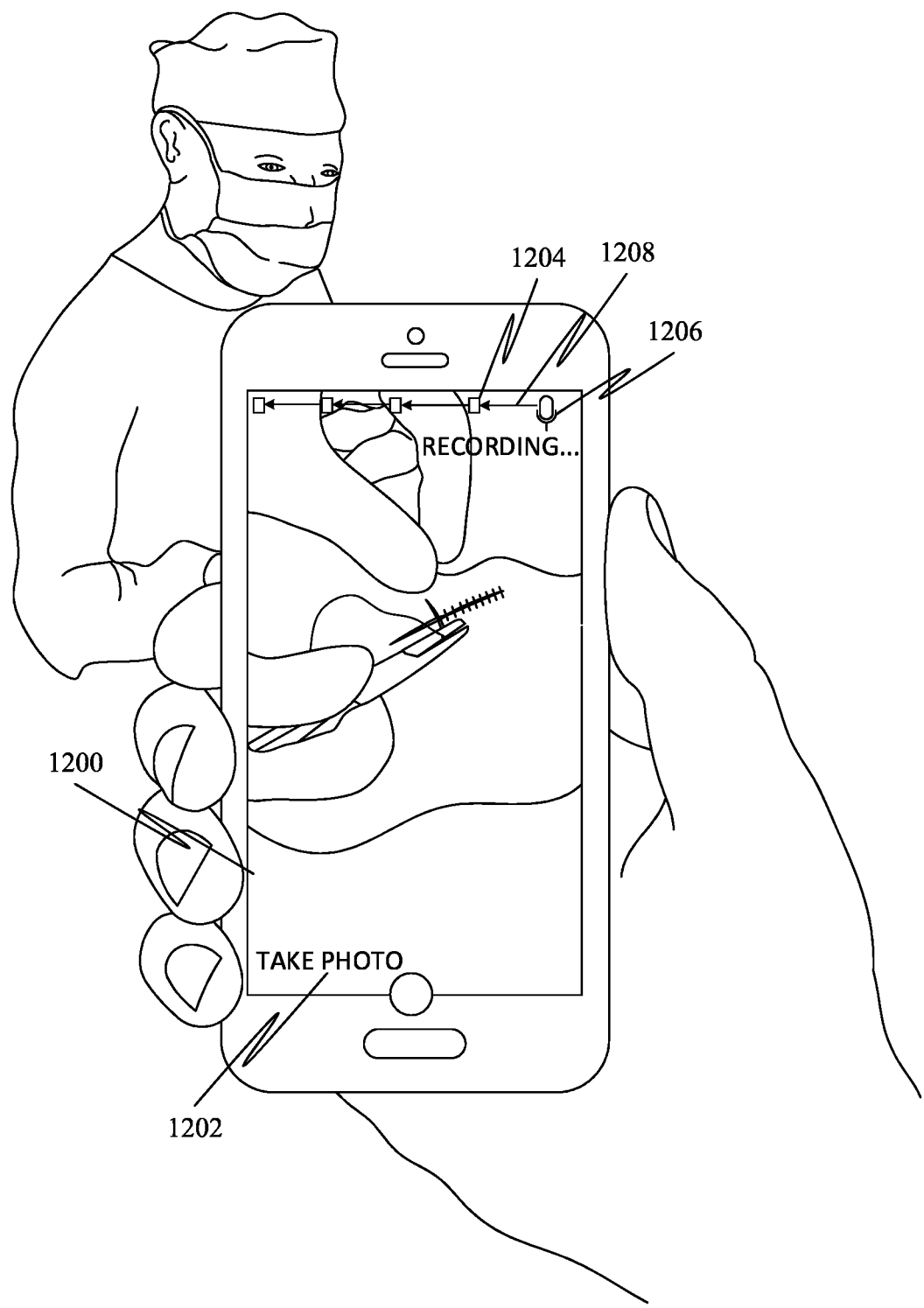
FIG. 13 is a screenshot of the user interface associated with the software application, in accordance with some embodiments.

FIG. 13 is a screenshot of the user interface 1200 associated with the software application, in accordance with some embodiments. Accordingly, an image shown in the user interface 1200 corresponds to stitching by a medical professional.

Figure 14:
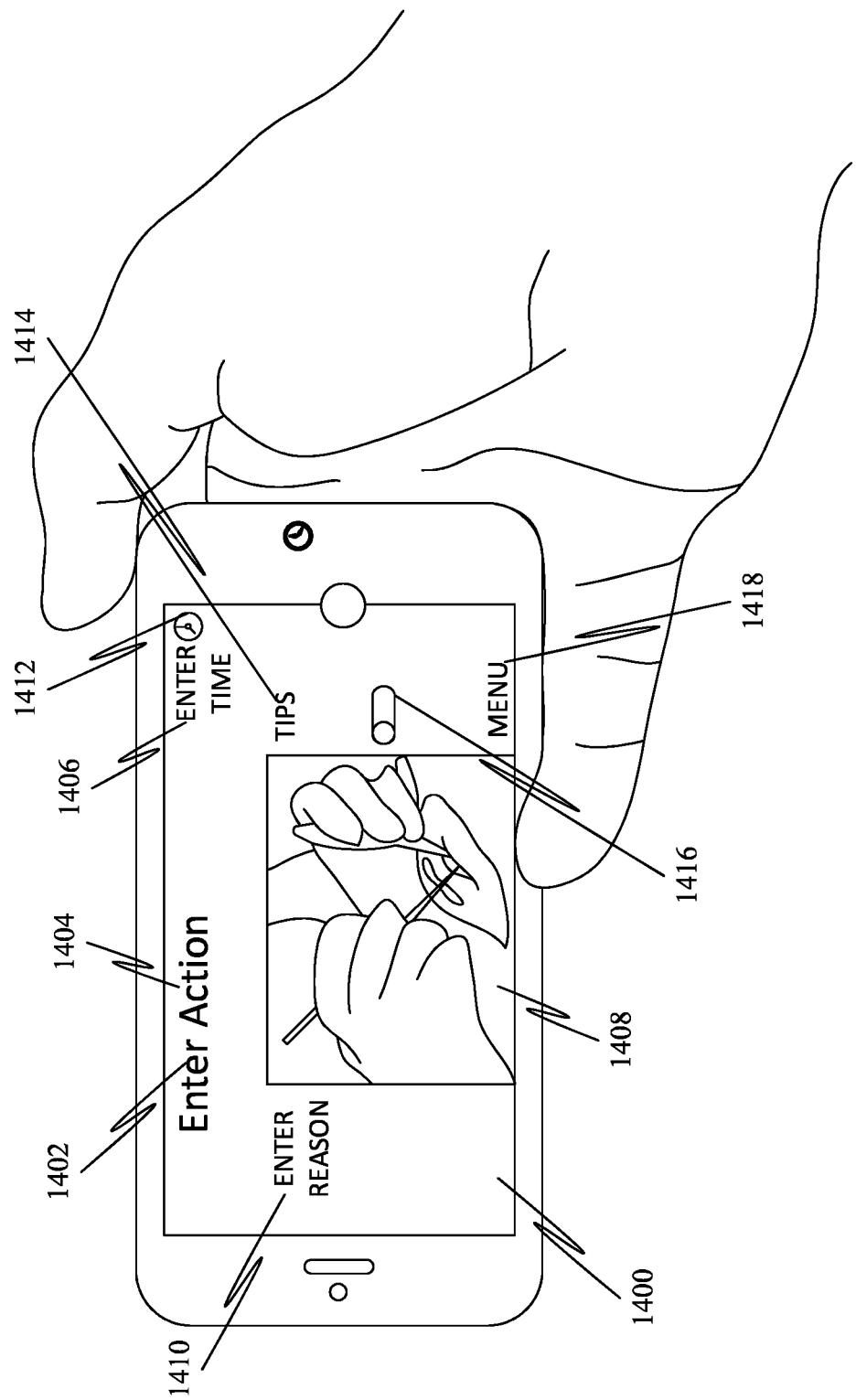
FIG. 14 is a screenshot of a user interface associated with the software application, in accordance with some embodiments.

FIG. 14 is a screenshot of a user interface 1400 associated with the software application, in accordance with some embodiments. Accordingly, the user interface 1400 may depict entry of metadata which prompts the user to describe each visualization (either photograph or video) using five core components: the action that included in the photo or video; the reason for performing the act a certain way; a warning for future users on how not to perform the act; pointers on things that future users should be aware of; and how long the act should take.

Once users have captured the image or video that is required in the tutorial, the user is prompted to enter written instructions to accompany each step. Before entering the written instructions, a section 1408 of the user interface 1400 may facilitate reviewing the captured image or video, as well as the accompanying audio by the user. Further, a section 1402 and a section 1404 of the user interface 1400 may facilitate entering of description of a step by the user. The information in the section 1404 is emphasized since it prompts the user to enter a verb as a one-word description of that particular step. Further, a section 1410 of the user interface 1400 may facilitate the users to enter the general-purpose that the step should achieve. Further, a section 1406 may facilitate viewing of the duration of the step by the user, as it was algorithmically calculated by the invention. A visualization of the time for each step is also apparent in a section 1412 of the user interface 1400.

Further, a section 1414 of the user interface 1400 may facilitate entering of additional descriptive information such as tips on accomplishing each step and things to be aware of. Further, a section 1416 of the user interface 1400 may the users to also upload images/videos of incorrect ways of completing each step so that anyone viewing the tutorial will be able to compare what they should do with what they should not do. Further, a section 1418 of the user interface 1400 may allow the users to access the general software menu.

Further, the section 1404 may include a succinct verb. Further, the section 1402 may include an object action. Further, the section 1410 may include a reason. Further, the section 1416 may include an option to append visualization alternative failure, for example, what not to do. Further, the section 1406 may include an additional descriptive information, for example, tips. Further, the section 1406 may include a duration of the step. Further, the section 1412 may include a time icon. Further, the section 1414 may include an additional descriptive information/advice: "Tips", "Do's, Do not's", "Always' or Nevers'". Further, the section 1416 may include an option to toggle between good (green) and bad (red) visualization of correct action. Further, the section 1418 may include a software menu.

Figure 15:
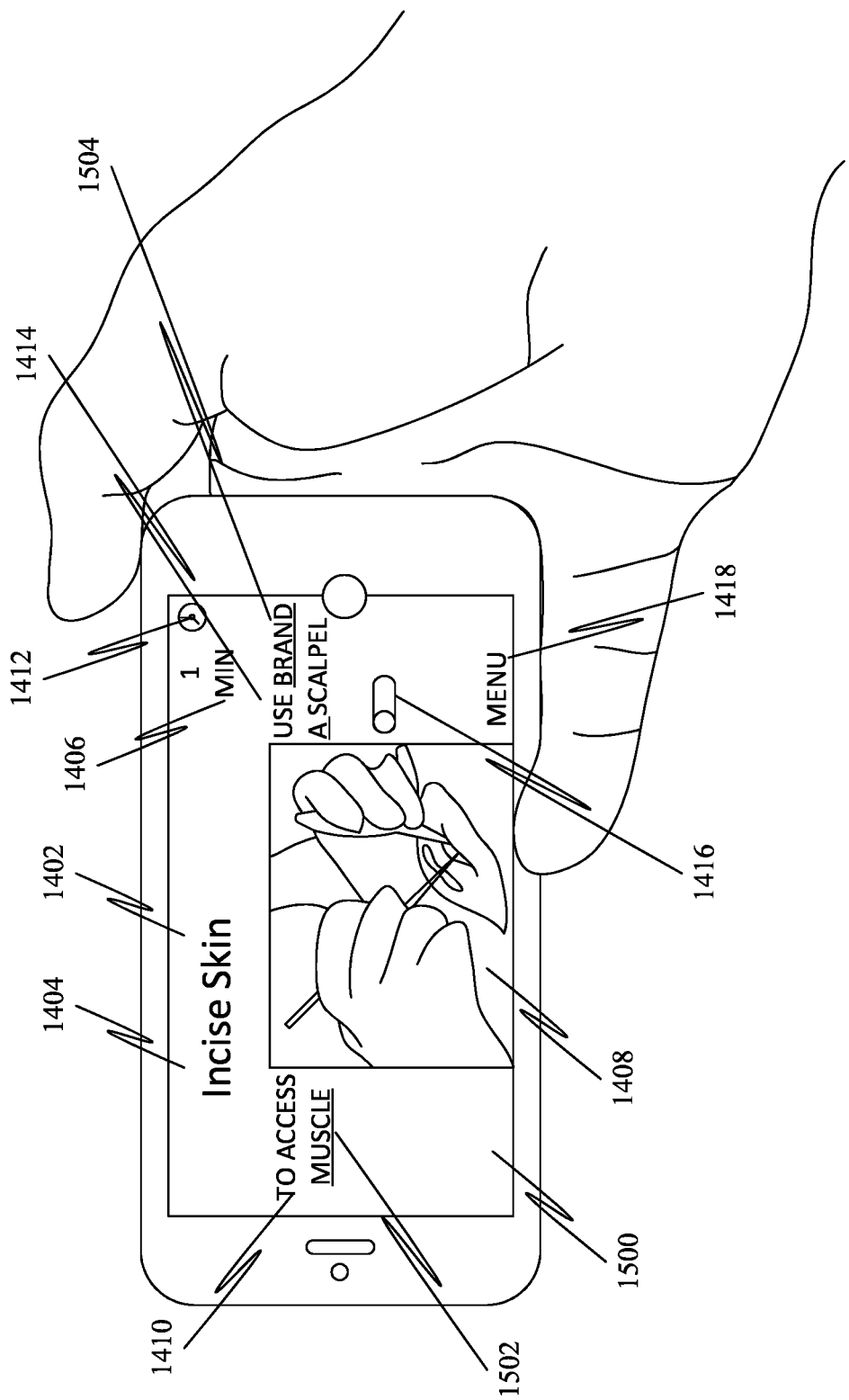
FIG. 15 is a screenshot of a user interface associated with the software application, in accordance with some embodiments.

FIG. 15 is a screenshot of a user interface 1500 associated with the software application, in accordance with some embodiments. Accordingly, a section 1502 of the user interface 1500 may allow the users to have the option to link reference material that may be helpful. Further, a section 1504 of the user interface 1500 may allow the users to link relevant metadata, such as safety information about the materials used, options to re-order materials, or affiliated advertisements. Further, the section 1502 may include an example of Hyperlink-able metadata such as URLs, PDFs, or other references. Further, the section 1504 may include an example to hyperlink to metadata pertaining suggested materials: relevant affiliate advertisements, options to order said items, or material safety information.

Figure 16:
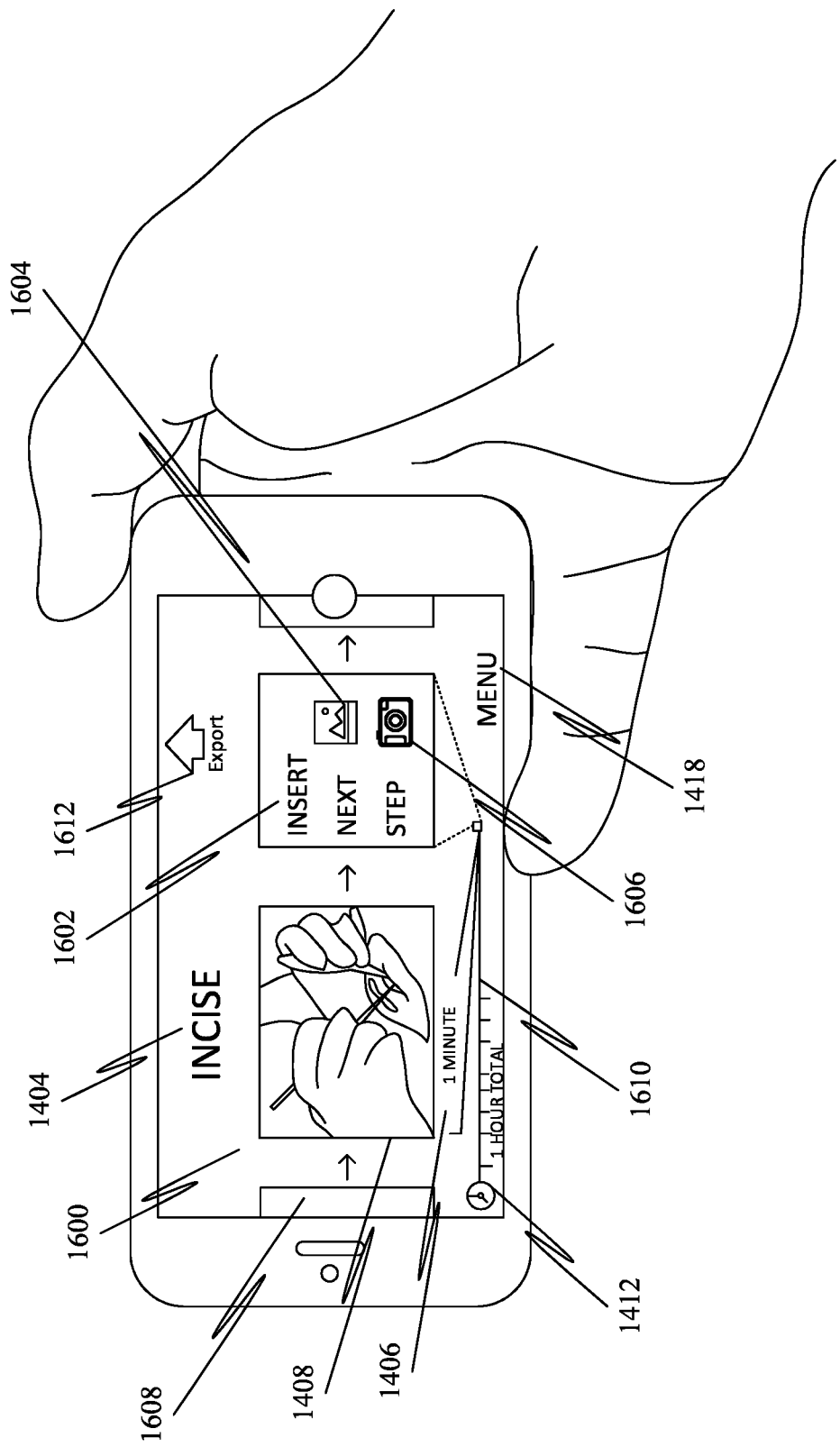
FIG. 16 is a screenshot of a user interface associated with the software application, in accordance with some embodiments.

FIG. 16 is a screenshot of a user interface 1600 associated with the software application, in accordance with some embodiments. Further, the user interface 1600 may illustrate a navigable and alterable overview of a time-successive captured method. If the user has entered all the relevant information for a particular step, a section 1602 of the user interface 1600 prompts the user to insert the next image/video of the tutorial. Further, a section 1604 may allow the user to select an image that is already stored on the user's smartphone. Further, a section 1606 of the user interface 1600 may allow the user to insert the next image/video of the tutorial through the smartphone's camera. If the user needs to return to a previous step, the user can do so by clicking a section 1608 of the user interface 1600. Further, a section 1610 of the user interface 1600 may allow the user to access the cumulative duration of the tutorial. If the user is pleased with the tutorial as is, the user can use a section 1612 of the user interface 1600 to export the tutorial.

Further, the section 1602 may include a cue to append next step in successive method recreation. Further, the section 1604 may include a cue to import next step visualization from storage. Further, the section 1606 may include a cue to import next step visualization from camera. Further, the section 1608 may include previous steps accessible and editable by finger-swipe and -tap. Further, the section 1610 may include a visualization of insofar total method duration and proportional step duration. Further, the section 1612 may include a cue to Export Method as is and Advance to FIG. 17.

Figure 17:
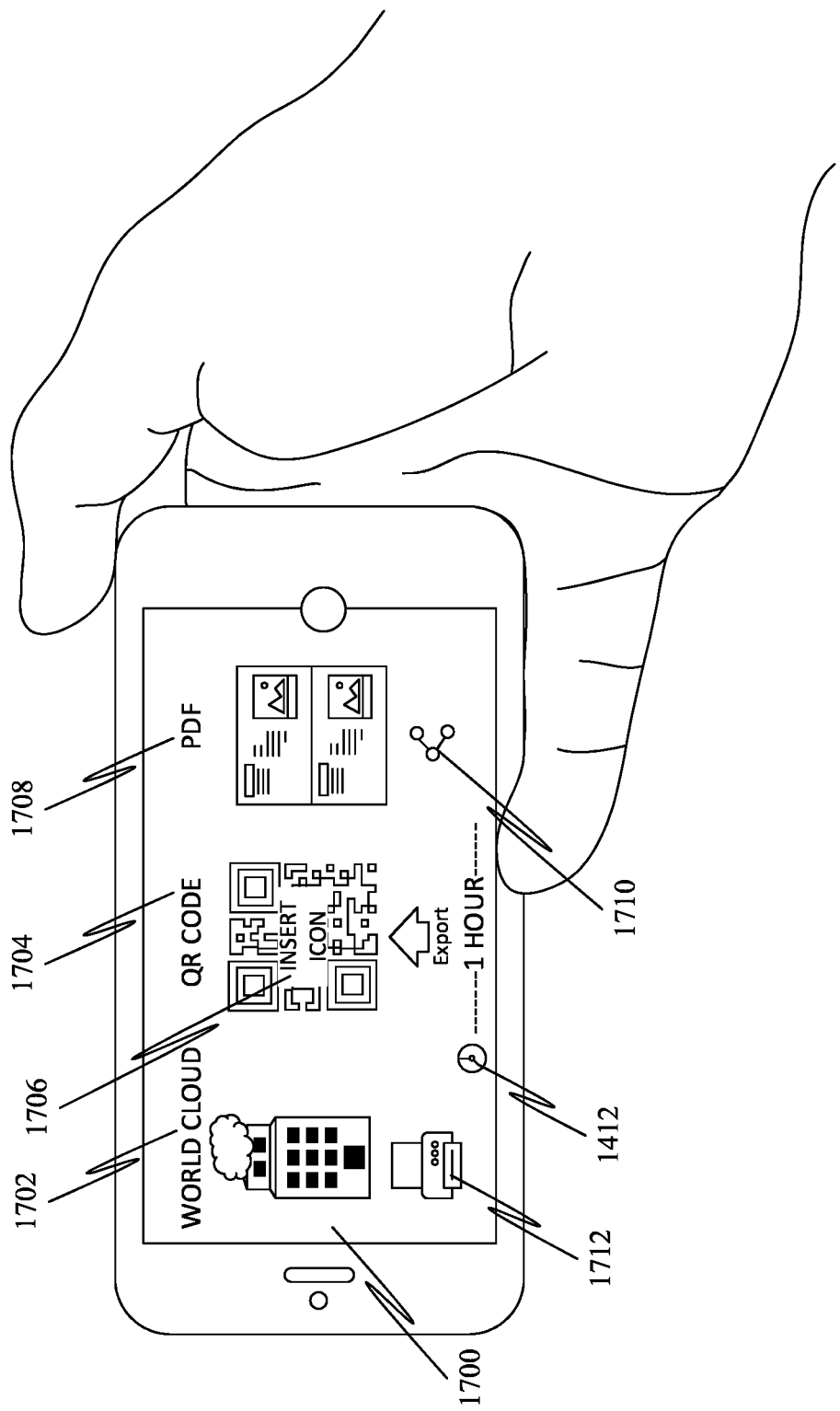
FIG. 17 is a screenshot of a user interface associated with the software application, in accordance with some embodiments.

FIG. 17 is a screenshot of a user interface 1700 associated with the software application, in accordance with some embodiments. Accordingly, the software application is configured for exporting/sharing the capture of the demonstrated method (such as surgery) using an audio-visual recording capable portable electronic device such as smartphone.

Further, a section 1702 of the user interface 1700 may allow the user to export the tutorial to workplace cloud data storage or a private server. Further, a section 1704 of the user interface 1700 may allow the user to export a printable QR code to accompany the tutorial. If the user does not have an existing QR code, he or she can create and insert a QR code using a section 1706 of the user interface 1700. Further, a section 1708 of the user interface 1700 may allow the user to convert the tutorial into PDF format, upon completion of the tutorial. Further, a section 1710 of the user interface 1700 may allow the user to share the tutorial through the available sharing options that are specific to each type of smartphone. Further, a section 1712 of the user interface 1700 may allow the user to print the tutorial.

Further, the section 1702 may facilitate exporting to workplace cloud data storage or private server. Further, the section 1704 may facilitate exporting Printable QR Code. Further, the section 1706 may facilitate creating and inserting a representative icon for the QR Code. Further, the section 1708 may facilitate converting method into a portable document file (pdf) printable format. Further, the section 1710 may facilitate sharing method via smartphone-mediated means. Further, the section 1712 may facilitate printing the method.

Figure 18:
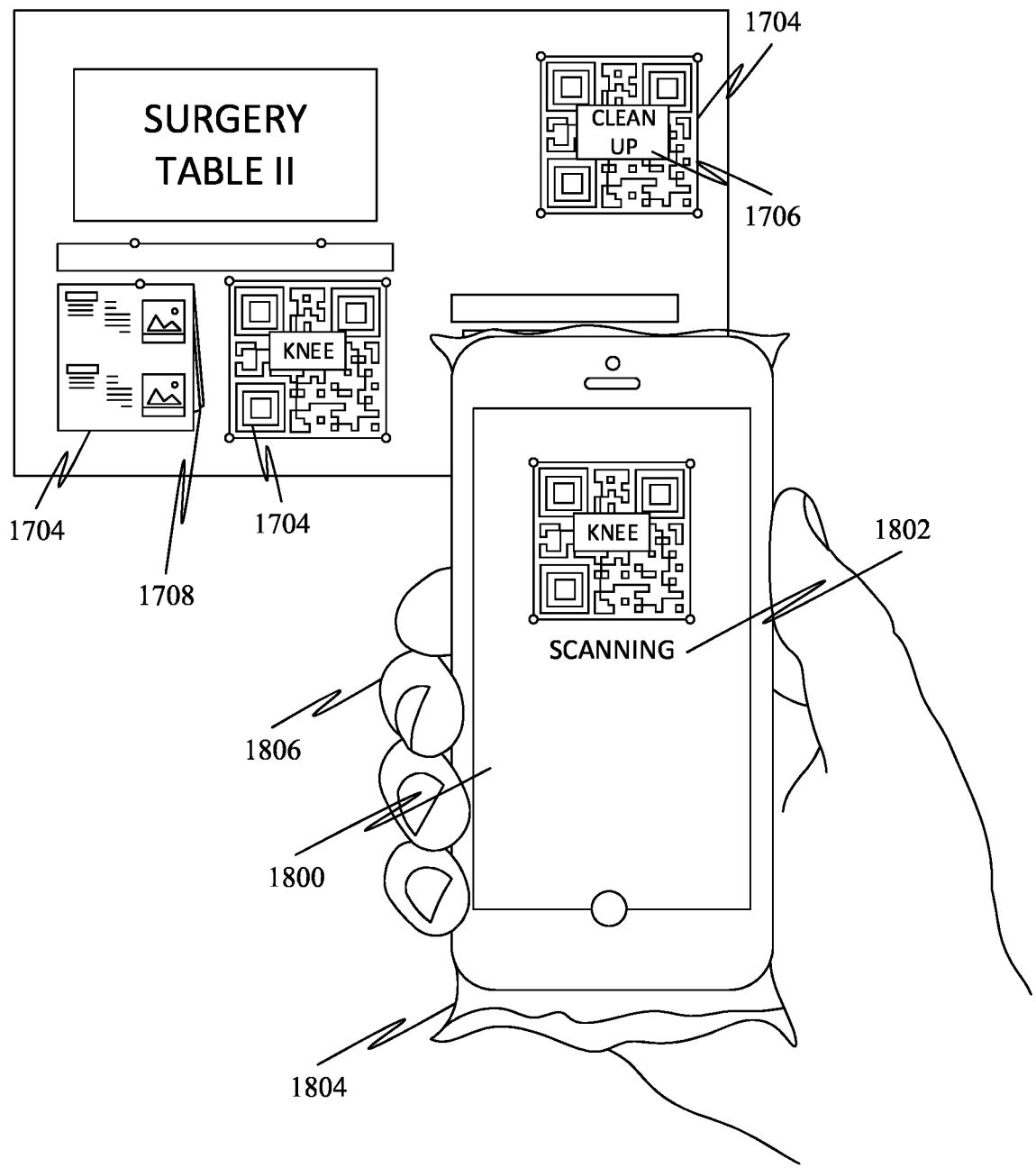
FIG. 18 is a screenshot of a user interface associated with the software application, in accordance with some embodiments.

FIG. 18 is a screenshot of a user interface 1800 associated with the software application, in accordance with some embodiments. Accordingly, the software application may facilitate scanning environment-relevant QR codes using a smartphone. Further, a section 1802 of the user interface 1800 may facilitate depiction of the software application instantly recognizing, scanning, and loading QR code associated method. Further, the mobile device may include a protective coating adapting portable device 1804 for hazardous environments. Further, the user may wear a touch-screen capable surgical glove 1806.

Figure 19:
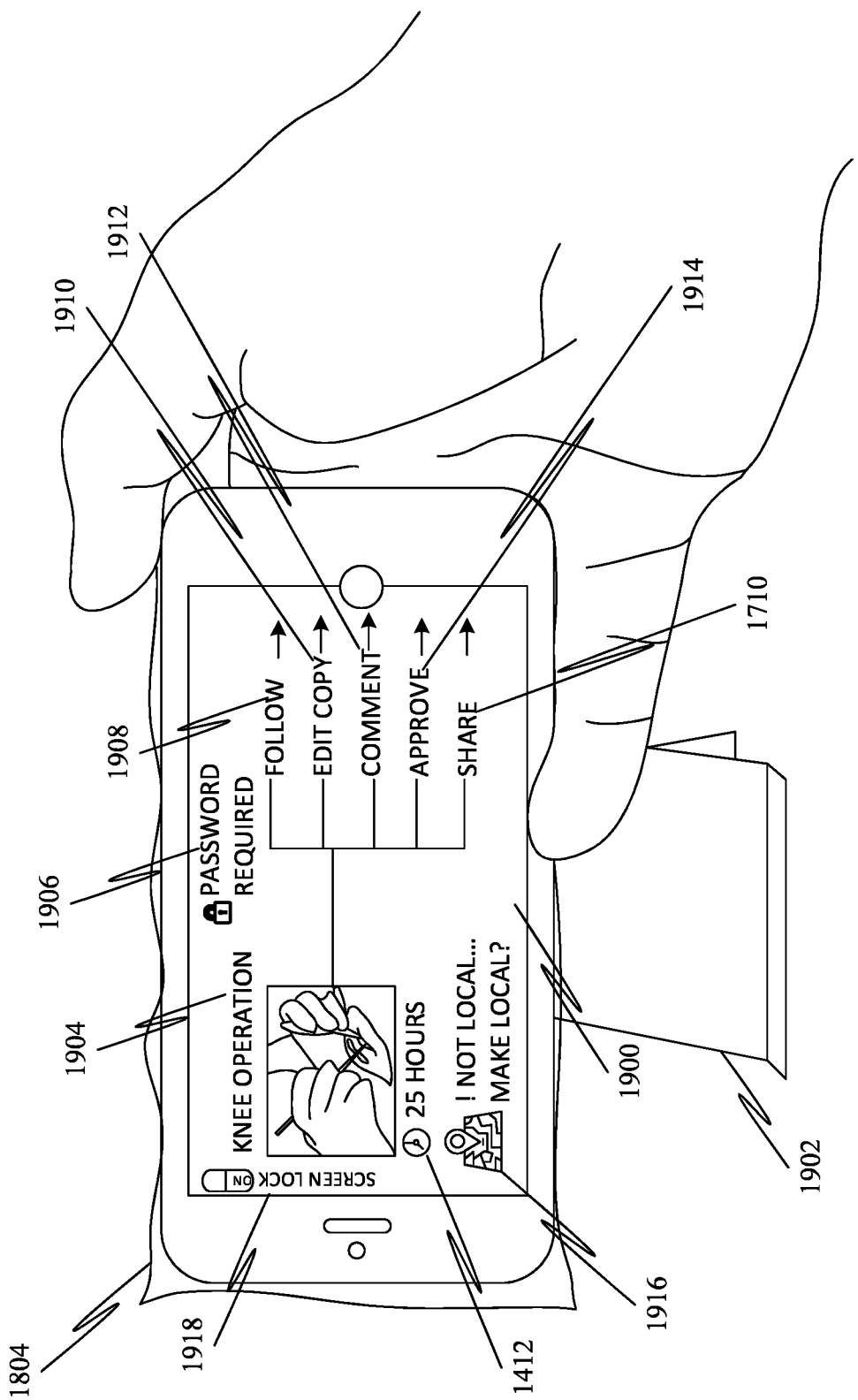
FIG. 19 is a screenshot of a user interface associated with the software application, in accordance with some embodiments.

FIG. 19 is a screenshot of a user interface 1900 associated with the software application, in accordance with some embodiments. Further, the user interface 1900 may illustrate uploading the instructional pictures and videos that were captured, as well as the various options that accompany each tutorial. Further, the software application may allow the user to tailor each tutorial to its resident environment by either localizing each step to a map or by duplicating the tutorial to replace certain components with those that are better suited to that particular environment. Further, the user may use a phone stand 1902 at an operating table. Further, if the user needs to modify the tutorial, this can be done in a number of ways. Further, a section 1904 of the user interface 1900 may allow the user to change the name of the tutorial. Further, a section 1906 of the user interface 1900 may allow the user to indicate whether the tutorial will be password protected. If the user is interested in changing the methodology used within the tutorial, a section 1908 of the user interface 1900 may allow the user to run through the current steps of the tutorial. Further, a section 1910 of the user interface 1900 may allow the user to edit a duplication of the tutorial. Further, a section 1912 of the user interface 1900 may allow the user to comment on the tutorial. Further, a section 1914 of the user interface 1900 may allow the user to review/approve of the tutorial's methodology. Further, a section 1916 of the user interface 1900 may allow the user to localize the tutorial to a specific environment. Further, a section 1918 of the user interface 1900 may allow the user to lock the screen from dimming or becoming dark.

Further, the software application may allow the user to make the method more appropriately suited to the resident environment, by either localizing each step to a map and by editing a copy and replacing components with those better suited to the environment.

Figure 20:
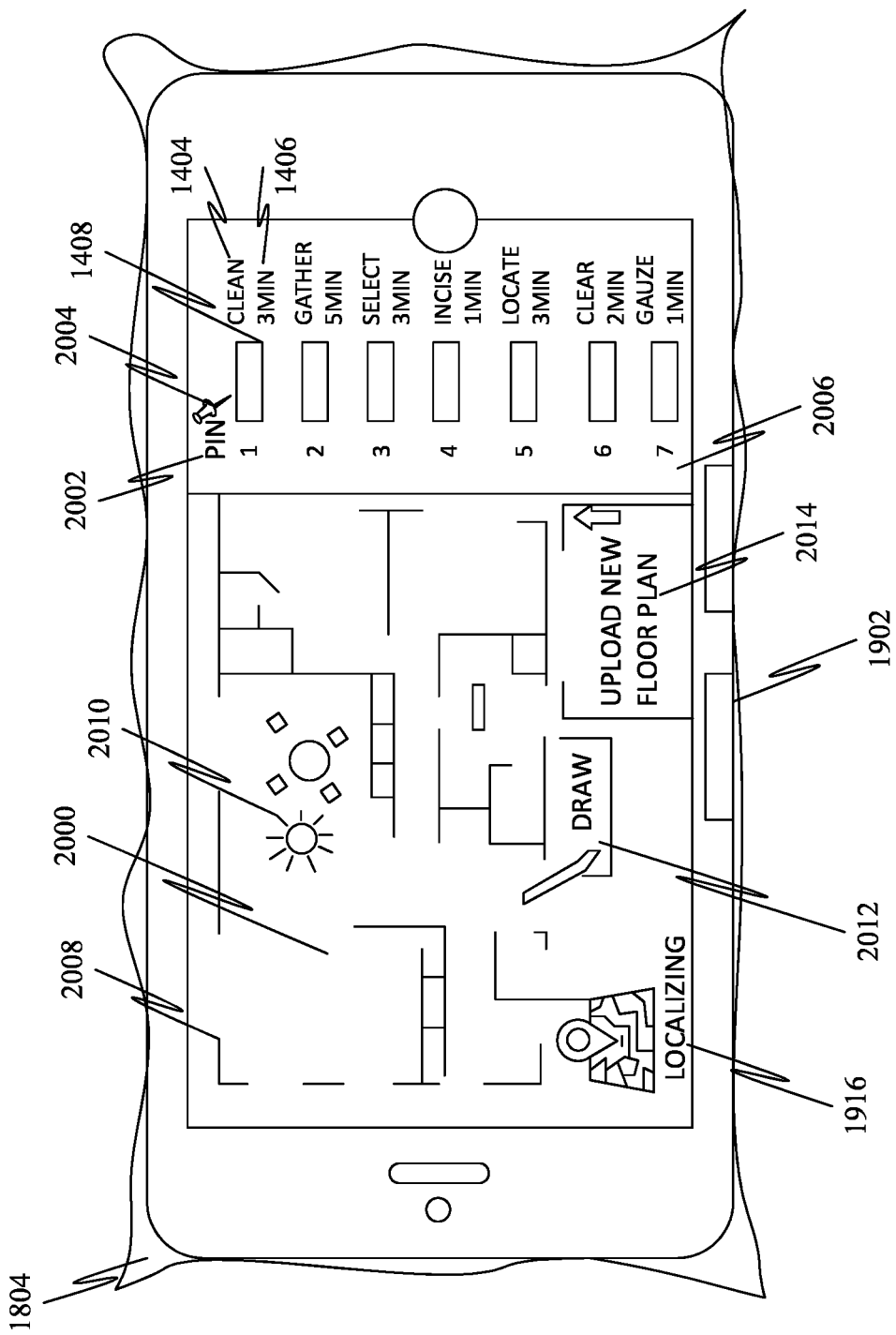
FIG. 20 is a screenshot of a user interface associated with the software application, in accordance with some embodiments.

FIG. 20 is a screenshot of a user interface 2000 associated with the software application, in accordance with some embodiments. Further, the user interface 2000 may illustrate localizing and pinning certain steps of the tutorial to the accompanying location on a floorplan in the relevant workspace. If the user elects to not localize the tutorial to a specific environment, at least one of a section 2002 and a section 2004 of the user interface 2000 may allow the user to user can pin certain steps and materials to specific locations within the relevant environment. In doing so, the user will be prompted to either upload or draw the floorplan of the relevant environment using a section 2008 of the user interface 2000. If changes to the floorplan are necessary, the user can make these changes using a section 2012 or can upload an image of the floorplan using a section 2014 of the user interface 2000. Further, a section 2006 of the user interface 2000 may include an automated number to be pinned to floorplan for cross-referential step identification. Further, a section 2010 of the user interface 2000 may facilitate location-enabled user tracking.

Further, the section 2002 may include a cue to pin below steps and potentially materials onto relevant environment. Further, the section 2004 may include a pin for placing steps and potentially materials onto relevant environment. Further, the section 2012 may allow the user to draw, update, or amend current floorplan with drawn equipment or workplace changes.

Figure 21:
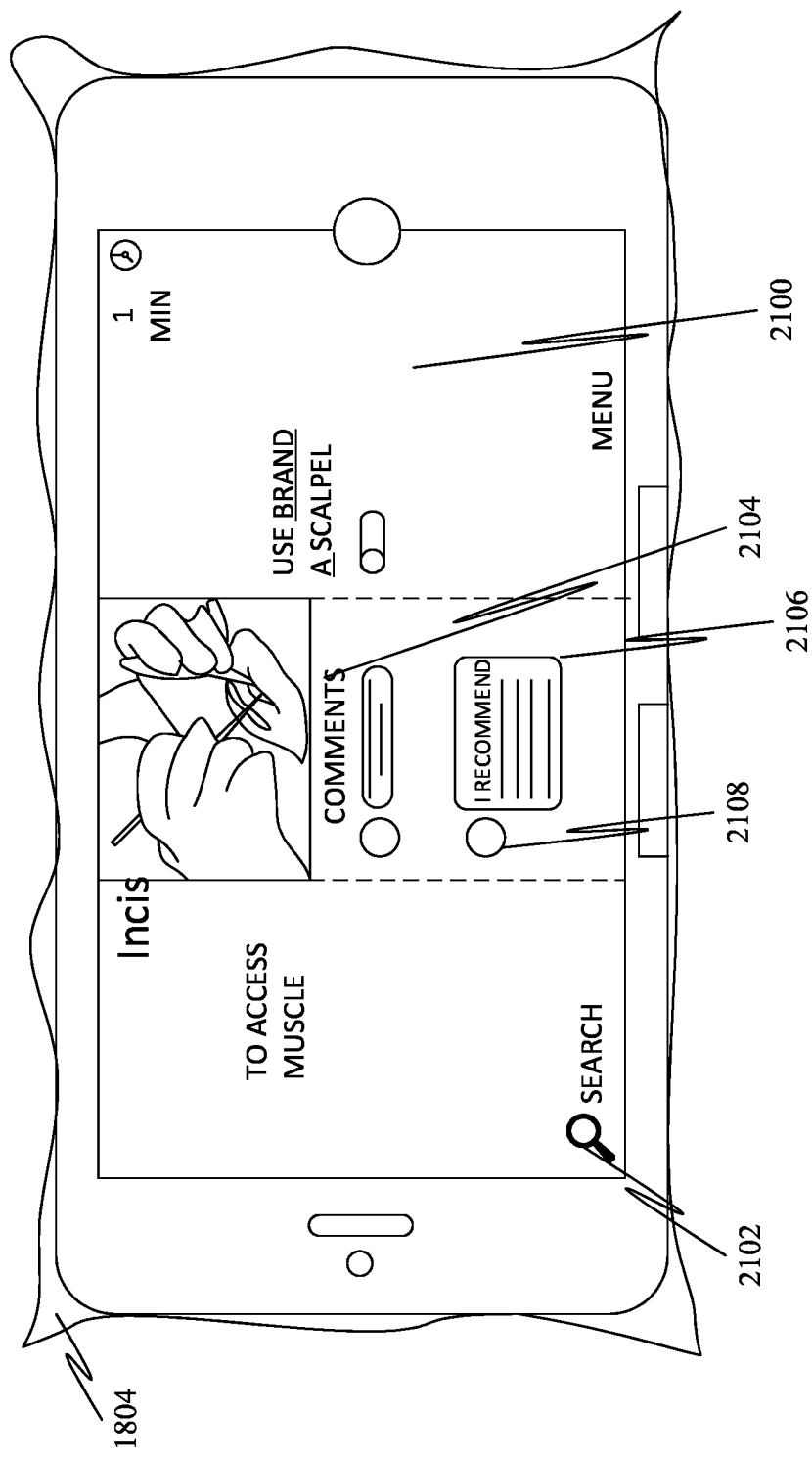
FIG. 21 is a screenshot of a user interface associated with the software application, in accordance with some embodiments.

FIG. 21 is a screenshot of a user interface 2100 associated with the software application, in accordance with some embodiments. Further, the user interface 2100 may depict a social network and user account capacities that allow for user recommendations, supervisor approvals, and/or corrective mechanisms. Further, the software application may facilitate finding a relevant data within a specific tutorial. Further, a section 2102 of the user interface 2100 may allow the user to search for a specific step within a tutorial. Further, a section 2104 of the user interface 2100 may allow the user to view all the commentary associated with each step in the tutorial. Further, a section 2106 of the user interface 2100 may include an example of user profile image. Further, a section 2108 of the user interface 2100 may include an example of user-associated comment pertaining to the above methodological step.

Further, the section 2102 may allow the user to performed a focused search of steps or information within the displayed method. Further, the section 2104 may include a list of comments, per methodological step.

Figure 22:
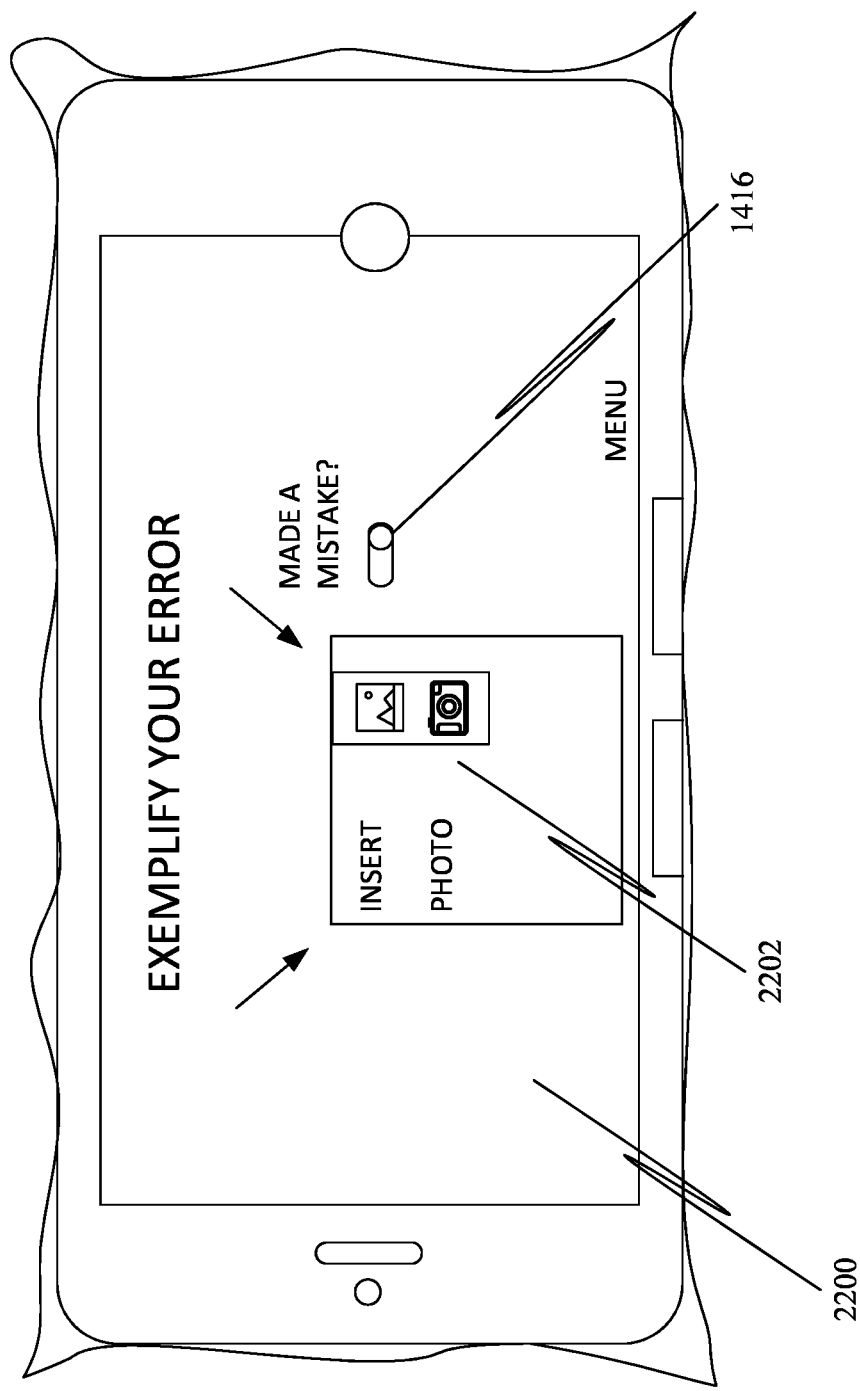
FIG. 22 is a screenshot of a user interface associated with the software application, in accordance with some embodiments.

FIG. 22 is a screenshot of a user interface 2200 associated with the software application, in accordance with some embodiments. Further, the user interface 2200 may allow the users to visually update tutorials to either rectify errors or insert warnings on what to be aware of during each step in the tutorial. Further, a section 2202 of the user interface 2200 may include an image or video space for recorded, exemplified mistakes as warnings to others.

Figure 23:
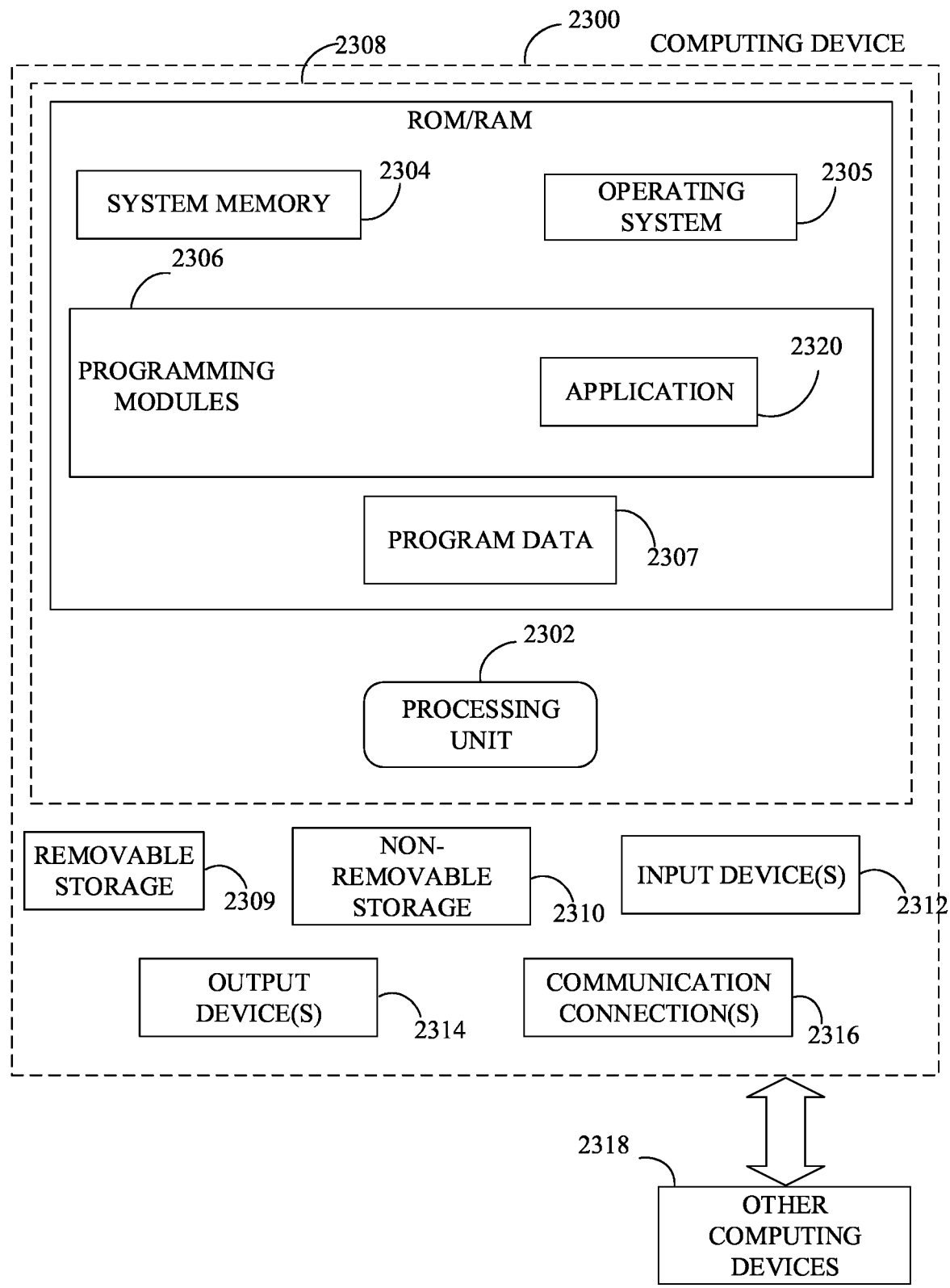
FIG. 23 is a block diagram of a computing device for implementing the methods disclosed herein, in accordance with some embodiments.

With reference to FIG. 23, a system consistent with an embodiment of the disclosure may include a computing device or cloud service, such as computing device 2300. In a basic configuration, computing device 2300 may include at least one processing unit 2302 and a system memory 2304. Depending on the configuration and type of computing device, system memory 2304 may comprise, but is not limited to, volatile (e.g. random-access memory (RAM)), non-volatile (e.g. read-only memory (ROM)), flash memory, or any combination.

System memory 2304 may include operating system 2305, one or more programming modules 2306, and may include a program data 2307. Operating system 2305, for example, may be suitable for controlling computing device 2300's operation. In one embodiment, programming modules 2306 may include image-processing module, machine learning module. Furthermore, embodiments of the disclosure may be practiced in conjunction with a graphics library, other operating systems, or any other application program and is not limited to any particular application or system. This basic configuration is illustrated in FIG. 23 by those components within a dashed line 2308.

Computing device 2300 may have additional features or functionality. For example, computing device 2300 may also include additional data storage devices (removable and/or non-removable) such as, for example, magnetic disks, optical disks, or tape. Such additional storage is illustrated in FIG. 23 by a removable storage 2309 and a non-removable storage 2310. Computer storage media may include volatile and non-volatile, removable and non-removable media implemented in any method or technology for storage of information, such as computer-readable instructions, data structures, program modules, or other data. System memory 2304, removable storage 2309, and non-removable storage 2310 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 2300. Any such computer storage media may be part of device 2300. Computing device 2300 may also have input device(s) 2312 such as a keyboard, a mouse, a pen, a sound input device, a touch input device, a location sensor, a camera, a biometric sensor, etc. Output device(s) 2314 such as a display, speakers, a printer, etc. may also be included. The aforementioned devices are examples and others may be used.

Computing device 2300 may also contain a communication connection 2316 that may allow device 2300 to communicate with other computing devices 2318, such as over a network in a distributed computing environment, for example, an intranet or the Internet. Communication connection 2316 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 2304, including operating system 2305. While executing on processing unit 2302, programming modules 2306 (e.g., application 2320 such as a media player) may perform processes including, for example, one or more stages of methods, algorithms, systems, applications, servers, databases as described above. The aforementioned process is an example, and processing unit 2302 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

The following is claimed:

1. A system for facilitating creating of customizable tutorials for instruments specific to a particular facility, the system comprising:
a communication device configured for:
providing a screen for capturing tutorial information, wherein the screen includes a list of facility blueprint input methods, vendors, and safety information associated with using at least one instrument;
prompting entry of a selection of one of the facility blueprint input methods and vendors, wherein the facility blueprint input methods include a drawing method and an inserting method;
accepting, at the screen, entry of a selected method and a selected vendor;
providing a screen on at least one user device for drawing the facility blueprint and accepting, at the screen, entry of a drawn facility blueprint if the selected method is the drawing method;
providing a screen on the at least one user device for inserting the facility blueprint and accepting, at the screen, entry of an inserted facility blueprint if the selected method is the inserting method;
receiving the facility blueprint from the at least one user device, wherein the facility blueprint facilitates locating the at least one instrument disposed in the facility, wherein the facility blueprint includes at least one relocatable instrument image;
taking a photo of each step of at a plurality of tutorial information and entering a duration of each step;
displaying the photo on the at least one user device;
receiving an actual instrument location of an instrument associated with the facility blueprint from the at least one user device;
providing a screen for user to select the at least one relocatable instrument image and relocate the at least one relocatable instrument image within the facility blueprint so that the at least one relocatable instrument image appears on the actual instrument location in the facility blueprint;
capturing, by using a camera or microphone, a timestamp, at least one visual or aural information to create a plurality of tutorial information,
creating a plurality of tutorial information based on the visual or aural information and the timestamp by using the at least one user device configured to receive the actual instrument location from a GPS receiver and associate the actual instrument location with the visual or aural information and timestamp, providing a sequential information of the plurality of tutorial information, by using the at least one user device that tracks time and the actual instrument location information from the GPS receiver, and a storage device configured for storing the plurality of tutorial information associated with the instrument corresponding to the instrument location.

2. The system of claim 1, wherein the communication device is further configured for:

transmitting the facility blueprint to at least one first user device;

receiving an instrument indication corresponding to an instrument of the at least one instrument from the at least one first user device; and transmitting a plurality of tutorial information associated with the instrument to the at least one first user device, wherein the at least one first user device is configured for presenting the plurality of tutorial information, wherein the storage device is configured for retrieving the plurality of tutorial information associated with the instrument based on the instrument indication.

3. The system of claim 1 further comprising a processing device communicatively coupled with the communication device and the storage device, wherein the communication device is configured for receiving at least one user information from the at least one user device, wherein, the processing device is configured for:

analyzing the plurality of tutorial information based on the at least one user information; and generating a plurality of new tutorial information corresponding to the plurality of tutorial information based on the analyzing, wherein the storage device is configured for storing the plurality of new tutorial information associated with the instrument corresponding to the instrument location.

4. The system of claim 1, wherein the at least one user device is configured for generating the plurality of tutorial information.

5. The system of claim 1 further comprising a processing device communicatively coupled with the communication device, wherein the communication device is configured for:

receiving at least one feedback associated with the plurality of tutorial information from the at least one user device; and transmitting a rating to the at least one user device, wherein the processing device is configured for:

analyzing the at least one feedback; and generating the rating for the plurality of tutorial information based on the analyzing.

6. The system of claim 1 further comprising a processing device communicatively coupled with the communication device and the storage device, wherein the communication device is further configured for receiving an instrument location request associated with the instrument from the at least one user device, wherein the processing device is configured for:

analyzing the instrument location request; and determining a new instrument location of the instrument associated with the facility blueprint based on the analyzing, wherein the storage device is configured for storing the plurality of tutorial information associated with the instrument corresponding to the new instrument location.

7. The system of claim 1 further comprising a processing device communicatively coupled with the communication device and the storage device, wherein the processing device is configured for:

identifying a plurality of tutorial metadata associated with the plurality of tutorial information; and analyzing the plurality of tutorial information based on the plurality of tutorial metadata, wherein the storage device is configured for storing the plurality of tutorial information associated with the instrument corresponding to the instrument location based on the analyzing.

8. The system of claim 1 further comprising a processing device communicatively coupled with the communication device and the storage device, wherein the communication device is configured for:

receiving a plurality of instrument information associated with the instrument from the at least one user device; and receiving a plurality of additional information corresponding to the plurality of instrument information from the at least one user device, wherein the processing device is configured for:

analyzing the plurality of instrument information and the plurality of additional information; and generating the plurality of tutorial information based on the analyzing.

9. The system of claim 1, wherein the plurality of tutorial information is characterized by at least one tutorial characteristic, wherein the at least one tutorial characteristic comprises at least one of a description, an instruction, and a duration.

10. The system of claim 1 further comprising a processing device communicatively coupled with the communication device and the storage device, wherein the communication device is configured for:

receiving at least one sensor data from at least one sensor, wherein the at least one sensor is configured for generating the at least one sensor data associated with the at least one instrument; and transmitting a plurality of tutorial information to the at least one user device, wherein the processing device is configured for:

analyzing the at least one sensor data; and identifying an instrument of the at least one instrument based on the analyzing, wherein the storage device is configured for retrieving the plurality of tutorial information based on the identifying.

11. A method for facilitating creating of customizable tutorials for instruments specific to a particular facility, the method comprising:

providing a screen for capturing tutorial information, wherein the screen includes a list of facility blueprint input methods, vendors, and safety information associated with using at least one instrument;

prompting entry of a selection of one of the facility blueprint input methods and vendors, wherein the facility blueprint input methods include a drawing method and an inserting method;

accepting, at the screen, entry of a selected method and a selected vendor;

providing a screen on at least one user device for drawing the facility blueprint and accepting, at the screen, entry of a drawn facility blueprint if the selected method is the drawing method;

providing a screen on the at least one user device for inserting the facility blueprint and accepting, at the screen, entry of an inserted facility blueprint if the selected method is the inserting method;

receiving the facility blueprint from the at least one user device, wherein the facility blueprint facilitates locating the at least one instrument disposed in the facility, wherein the facility blueprint includes at least one relocatable instrument image;

taking a photo of each step of a plurality of tutorial information and entering a duration of each step;

displaying the photo on the at least one user device;

receiving an actual instrument location of an instrument associated with the facility blueprint from the at least one user device;

providing a screen for user to select the at least one relocatable instrument image and relocate the at least one relocatable instrument image within the facility blueprint so that the at least one relocatable instrument image appears on the actual instrument location in the facility blueprint;

capturing, by using a camera or microphone, a timestamp, at least one visual or aural information to create a plurality of tutorial information, creating a plurality of tutorial information based on the visual or aural information and the timestamp by using the at least one user device configured to receive the actual instrument location from a GPS receiver and associate the actual instrument location with the visual or aural information and timestamp, providing a sequential information of the plurality of tutorial information, by using the at least one user device that tracks time and the actual instrument location information from the GPS receiver, and storing, using a storage device, the plurality of tutorial information associated with the instrument corresponding to the instrument location.

12. The method of claim 11 further comprising:
transmitting, using the communication device, the facility blueprint to at least one first user device;
receiving, using the communication device, an instrument indication corresponding to an instrument of the at least one instrument from the at least one first user device;
retrieving, using the storage device, a plurality of tutorial information associated with the instrument based on the instrument indication; and
transmitting, using the communication device, the plurality of tutorial information associated with the instrument to the at least one first user device, wherein the at least one first user device is configured for presenting the plurality of tutorial information.

13. The method of claim 11 further comprising:
receiving, using the communication device, at least one user information from the at least one user device;
analyzing, using a processing device, the plurality of tutorial information based on the at least one user information;
generating, using the processing device, a plurality of new tutorial information corresponding to the plurality of tutorial information based on the analyzing, and
storing, using the storage device, the plurality of new tutorial information associated with the instrument corresponding to the instrument location.

14. The method of claim 11, wherein the at least one user device is configured for generating the plurality of tutorial information.

15. The method of claim 11 further comprising:
receiving, using the communication device, at least one feedback associated with the plurality of tutorial information from the at least one user device;
analyzing, using a processing device, the at least one feedback;
generating, using the processing device, a rating for the plurality of tutorial information based on the analyzing; and
transmitting, using the communication device, the rating to the at least one user device.

16. The method of claim 11 further comprising:
receiving, using the communication device, an instrument location request associated with the instrument from the at least one user device;
analyzing, using a processing device, the instrument location request;
determining, using the processing device, a new instrument location of the instrument associated with the facility blueprint based on the analyzing; and
storing, using the storage device, the plurality of tutorial information associated with the instrument corresponding to the new instrument location.

17. The method of claim 11 further comprising:
identifying, using a processing device, a plurality of tutorial metadata associated with the plurality of tutorial information;
analyzing, using the processing device, the plurality of tutorial information based on the plurality of tutorial metadata; and
storing, using the storage device, the plurality of tutorial information associated with the instrument corresponding to the actual instrument location based on the analyzing.

18. The method of claim 11 further comprising:
receiving, using the communication device, a plurality of instrument information associated with the instrument from the at least one user device;
receiving, using the communication device, a plurality of additional information corresponding to the plurality of instrument information from the at least one user device;
analyzing, using a processing device, the plurality of instrument information and the plurality of additional information; and
generating, using the processing device, the plurality of tutorial information based on the analyzing.

19. The method of claim 11, wherein the plurality of tutorial information is characterized by at least one tutorial characteristic, wherein the at least one tutorial characteristic comprises at least one of a description, an instruction, and a duration.

20. The method of claim 11 further comprising:
receiving, using the communication device, at least one sensor data from at least one sensor, wherein the at least one sensor is configured for generating the at least one sensor data associated with the at least one instrument;
analyzing, using a processing device, the at least one sensor data; and
identifying, using the processing device, an instrument of the at least one instrument based on the analyzing;
retrieving, using the storage device, a plurality of tutorial information associated with the instrument based on the identifying; and transmitting, using the communication device, the plurality of tutorial information to the at least one user device.

\* \* \* \* \*